US012428626B2

(12) United States Patent
Liu

(10) Patent No.: US 12,428,626 B2
(45) Date of Patent: Sep. 30, 2025

(54) CELLS FOR THE PRODUCTION OF VIRUSES AND METHODS OF USING THE SAME

(71) Applicant: BioVentures, LLC, Little Rock, AR (US)

(72) Inventor: Jia Liu, Little Rock, AR (US)

(73) Assignee: BioVentures, LLC, Little Rock, AR (US)

( * ) Notice: Subject to any disclaimer, the term of this patent is extended or adjusted under 35 U.S.C. 154(b) by 1042 days.

(21) Appl. No.: 17/295,761

(22) PCT Filed: Nov. 20, 2019

(86) PCT No.: PCT/US2019/062470
§ 371 (c)(1),
(2) Date: May 20, 2021

(87) PCT Pub. No.: WO2020/106880
PCT Pub. Date: May 28, 2020

(65) Prior Publication Data
US 2022/0010285 A1    Jan. 13, 2022

Related U.S. Application Data

(60) Provisional application No. 62/769,834, filed on Nov. 20, 2018.

(51) Int. Cl.
*C12N 7/00* (2006.01)
*C12N 9/22* (2006.01)
*C12N 15/11* (2006.01)

(52) U.S. Cl.
CPC .................. *C12N 7/00* (2013.01); *C12N 9/22* (2013.01); *C12N 15/111* (2013.01); *C12N 2710/24052* (2013.01)

(58) Field of Classification Search
None
See application file for complete search history.

(56) References Cited

U.S. PATENT DOCUMENTS

| | | |
|---|---|---|
| 7,521,056 B2 | 4/2009 | Chang et al. |
| 7,527,787 B2 | 5/2009 | Chang et al. |
| 7,534,866 B2 | 5/2009 | Chang et al. |
| 7,550,143 B2 | 6/2009 | Chang et al. |
| 7,666,400 B2 | 2/2010 | Chang et al. |
| 8,227,440 B2 | 7/2012 | McFadden et al. |
| 8,512,713 B2 | 8/2013 | Barrett et al. |

FOREIGN PATENT DOCUMENTS

| | | |
|---|---|---|
| EP | 0453082 | 10/1991 |
| WO | 90/14837 | 12/1990 |
| WO | 2019/227022 | 11/2019 |
| WO | 2020/056424 | 3/2020 |

OTHER PUBLICATIONS

Nounamo B, Li Y, O'Byrne P, Kearney AM, Khan A, Liu J. An interaction domain in human SAM D9 is essential for myxoma virus host-range determinant M062 antagonism of host anti-viral function. Virology. Mar. 2017;503:94-102. doi: 10.1016/j.virol.2017.01.004. Epub Jan. 31, 2017. PMID: 2815762. (Year: 2017).*
Nounamo, et al. Virology. Mar. 2017;503:94-102. doi: 10.1016/j.virol.2017.01.004. Epub Jan. 31, 2017. PMID: 28157624 (Year: 2017).*
Smallwood, et al. Curr Protoc Microbiol. May 2010;Chapter 14: Unit 14A. 1. doi: 10.1002/9780471729259.mc14a01s17. PMID: 20440681. (Year: 2010).*
Wang, et al. Mar. 17, 2016:6:23205. doi: 10.1038/srep23205. (Year: 2016).*
Gregory, et al. J Virol. Dec. 2004;78(24):13582-90. doi: 10.1128/JVI.78.24.13582-13590.2004. PMID: 15564469. (Year: 2004).*
Colgrove, et al. Virology. Jan. 2016;487:215-21. doi: 10.1016/j.virol.2015.09.026. Epub Nov. 5, 2015. PMID: 26547038. (Year: 2016).*
Alleviating MDR-TB Treatment Side Effects in Botswana. <http://kncvtbc.org/en/project/alleviating-mdr-tb-treatment-side-effects-in-botswana/> (accessed Jan. 14)).
Ibrahim, N. et al. Barrier to autointegration factor (BAF) inhibits vaccinia virus intermediate transcription in the absence of the viral B1 kinase. Virology 2013, 444(1-2): 363-373.
Ibrahim, N. et al. Molecular characterization of the host defense activity of the barrierto autointegration factor against vaccinia virus. Journal of virology 2011, 85(22): 11588-11600.
International Search Report and Written Opinion for International Patent Application No. PCT/US2019/033973, dated Aug. 16, 2019.
International Search Report and Written Opinion for International Patent Application No. PCT/US2019/062470, dated Feb. 18, 2020.
Kane, M. et al. Identification of Interferon-Stimulated Genes with Antiretroviral Activity. Cell host & microbe 2016, 20(3): 392-405.
Karyampudi, L. et al. PD-1 Blunts the Function of Ovarian Tumor-Infiltrating Dendritic Cells by Inactivating NF-κB. Cancer Res. Jan. 15, 2016;76(2):239-50. doi: 10.1158/0008-5472.CAN-15-0748. Epub Nov. 13, 2015. PMID: 26567141; PMCID: PMC4715980.
Kaufman, H.L. et al. Oncolytic viruses: a new class of immunotherapy drugs. Nat. Rev. Drug Discov. 2015;14:642-662.
Keller, B.A. & Bell, J.C. Oncolytic viruses-immunotherapeutics on the rise. J. Mol. Med. (Berl.) 2016;94:979-991.
Kelley, L.A. et al. The Phyre2 web portal for protein modeling, prediction and analysis. Nature protocols 2015, 10(6): 845-858.
Kerr, P.J. et al. Evolutionary history and attenuation of myxoma virus on two continents. PLoS pathogens 2012, 8(10): e1002950.

(Continued)

*Primary Examiner* — Janet L Andres
*Assistant Examiner* — Jeffrey Mark Sifford
(74) *Attorney, Agent, or Firm* — Quarles & Brady, LLP

(57) ABSTRACT

The present disclosure provides compositions and methods for increasing the production of virus in vitro. Modified cells which are modified to eliminate or reduce as compared to a control cell the activity or expression of a Sterile α motif-domain containing protein 9 (SAMD9) polypeptide are provided. Methods of using these cells are also provided.

5 Claims, 7 Drawing Sheets

Specification includes a Sequence Listing.

(56) References Cited

OTHER PUBLICATIONS

Kerr, P.J. et al. Genome scale evolution of myxoma virus reveals host-pathogen adaptation and rapid geographic spread. J Virol. Dec. 2013; 87(23): 12900-12915.
Kerr, P.J. et al. Genomic and phenotypic characterization of myxoma virus from Great Britain reveals multiple evolutionary pathways distinct from those in Australia. PLoS pathogens 2017, 13(3): e1006252.
Kerr, P.J. Myxoma virus and the Leporipoxviruses: an evolutionary paradigm. Viruses 2015, 7(3): 1020-1061.
Klicher, S. et al. siRNA screen of early poxvirus genes identifies the AAA+ ATPase D5 as the virus genome-uncoating factor. Cell host & microbe 2014, 15(1): 103-112.
Knight, M.J. et al. A human sterile alpha motif domain polymerizome. Protein science : a publication of the Protein Society 2011, 20(10): 1697-1706.
Knutson, K.L. et al. Immunoediting of cancers may lead to epithelial to mesenchymal transition. J Immunol. Aug. 1, 2006;177(3):1526-33. doi: 10.4049/jimmunol.177.3.1526. PMID: 16849459.
Kolb, H.C. et al. Click Chemistry: Diverse Chemical Function from a Few Good Reactions. Angewandte Chemie International Edilion 2001, 40, 2004-2021.
Kovesdi, I. & Hedley, S.J. Adenoviral producer cells. Viruses. Aug. 2010;2(8):1681-1703. doi: 10.3390/v2081681. Epub Aug. 16, 2010. PMID: 21994701; PMCID: PMC3185730.
Kranzusch, P.J. et al. Ancient Origin of cGAS-STING Reveals Mechanism of Universal 2',3' cGAMP Signaling. Molecular cell 2015, 59(6): 891-903.
Kranzusch, P.J. et al. Structure of human cGAS reveals a conserved family of second-messenger enzymes in innate immunity. Cell reports 2013, 3(5): 1362-1368.
Kryczek, I. et al. B7-H4 expression identifies a novel suppressive macrophage population in human ovarian carcinoma. J Exp Med. Apr. 17, 2006;203(4):871-81. doi: 10.1084/jem.20050930. Epub Apr. 10, 2006. PMID: 16606666; PMCID: PMC2118300.
Lamichhane, P et al. IL10 Release upon PD-1 Blockade Sustains Immunosuppression in Ovarian Cancer. Cancer Res. Dec. 1, 2017;77(23):6667-6678. doi: 10.1158/0008-5472.CAN-17-0740. Epub Oct. 9, 2017. PMID: 28993412; PMCID: PMC5712245.
Lemos De Matos, A. et al. Evolution and divergence of the mammalian SAMD9/SAMD9L gene family. BMC evolutionary biology 2013, 13: 121.
Li, C.F. et al. Human sterile alpha motif domain 9, a novel gene identified as down-regulated in aggressive fibromatosis, is absent in the mouse. BMC Genomics. Apr. 3, 2007:8:92. doi: 10.1186/1471-2164-8-92.
Li, X-D, et al. Pivotal roles of cGAS-cGAMP signaling in antiviral defense and immune adjuvant effects. Science (New York, NY) 2013, 341(6152): 1390-1394.
Liu, J. & Mcfadden, G. SAMD9 is an innate antiviral host factor with stress response properties that can be antagonized by poxviruses. J Virol. Feb. 2015;89(3):1925-31. doi: 10.1128/JVI.02262-14. Epub Nov. 26, 2014.
Liu, J. et al. M062 Is a Host Range Factor Essential for Myxoma Virus Pathogenesis and Functions as an Antagonist of Host SAMD9 in Human Cells. J Virol. 85(7):3270-3282 (2011).
Liu, J. et al. Myxoma virus expressing interleukin-15 fails to cause lethal myxomatosis in European rabbits. Journal of virology 2009, 83(11): 5933-5938.
Liu, J. et al. Myxoma virus M064 is a novel member of the poxvirus C7L superfamily of host range factors that controls the kinetics of myxomatosis in European rabbits. J. Virol. 2012;86:5371-5375.
Liu, J. et al. Reduction in severity of a herpes simplex virus type 1 murine infection by treatment with a ribozyme targeting the UL20 gene RNA. Journal of virology 2008, 82(15): 7467-7474.
Liu, J. et al. The poxvirus C7L host range factor superfamily. Current opinion in virology 2012, 2(6): 764-772.

Loschke, F. et al. Keratin Isotypes Control Desmosome Stability and Dynamics through PKCalpha. The Journal of investigative dermatology 2016, 136(1): 202-213.
Luecke, S. et al. cGAS is activated by DNA in a length-dependent manner. EMBO reports 2017, 18(10): 1707-1715.
Macneill, A.L. et al. Mutation of the Myxoma virus SERP2 P1-site to prevent proteinase inhibition causes apoptosis in cultured RK-13 cells and attenuates disease in rabbits, but mutation to alter specificity causes apoptosis without reducing virulence. Virology 2006, 356(1-2): 12-22.
Maher, S.G. et al. IFNalpha and IFNlambda differ in their antiproliferative effects and duration of JAK/STAT signaling activity. Cancerbiology & therapy 2008, 7(7): 1109-1115.
Mankan, A.K. et al. Cytosolic RNA:DNA hybrids activate the cGAS-STING axis. The EMBO journal 2014, 33(24): 2937-2946.
Mcharg, S. et al. Down-regulation of desmosomes in cultured cells: the roles of PKC, microtubules and lysosomal/proteasomal degradation. PloS one 2014, 9(10): e108570.
Mekhedov, S.L. et al. The complex domain architecture of SAMD9 family proteins, predicted STAND-like NTPases, suggests new links to inflammation and apoptosis. Biology direct 2017, 12(1): 13.
Meng, X. et al. Structural basis for antagonizing a host restriction factor by C7 family of poxvirus host-range proteins. Proceedings of the National Academy of Sciences of the United States of America 2015, 112(48): 14858-14863.
Mercer, J. et al. RNAi screening reveals proteasome- and Cullin3-dependent stages in vaccinia virus infection. Cell reports 2012, 2(4): 1036-1047.
Meruelo, A.D. & Bowie, J.U. Identifying polymer-forming SAM domains. Proteins 2009, 74(1): 1-5.
Messud-Petit, F. et al. Serp2, an inhibitor of the interleukin-1beta-converting enzyme, is critical in the pathobiology of myxoma virus. J Virol. Oct. 1998; 72(10): 7830-7839.
Mezulis, S. et al. PhyreStorm: A Web Server for Fast Structural Searches Against the PDB. Journal of molecular biology 2016, 428(4): 702-708.
Moehler, M. et al. Activation of the human immune system by chemotherapeutic or targeted agents combined with the oncolytic parvovirus H-1. BMC Cancer. 2011;11:464.
Molodtsov, V. et al. Structural basis for rifamycin resistance of bacterial RNA polymerase by the three most clinically important RpoB mutations found in Mycobacteriwn tuberculosis. Molecular Microbiology 2017, 103, 1034-1045.
Molodtsov, V. et al. X-ray Crystal Structures of the *Escherichia coli* RNA Polymerase in Complex with Benzoxazinorifamycins. Journal of Medicinal Chemistry 2013, 56, 4758-4763.
Moo-Young, T.A. et al. Tumor-derived TGF-beta mediates conversion of CD4+Foxp3+ regulatory T cells in a murine model of pancreas cancer. J. Immunother. 2009;32:12-21.
Moss, B. & Filler, R. Irreversible effects of cycloheximide during the early period of vaccinia virus replicaon. J Virol. Feb. 1970; 5(2): 99-108.
Wang, F. et al. RIG-I mediates the co-induction of tumor necrosis factor and type I interferon elicited by myxoma virus in primary human macrophages. PLoS Pathog. 2008;4:e1000099.
Wang, G. et al. Infection of human cancer cells with myxoma virus requires Akt activation via interaction with a viral ankyrin-repeat host range factor. Proc. Natl. Acad. Sci. USA. 2006;103:4640-4645.
Wang, J. et al. Sterile alpha Motif Domain Containing 9 Is a Novel Cellular Interacting Partner to Low-Risk Type Human Papillomavirus E6 Proteins. PloS one 2016, 11(2): e0149859.
Wang, M. et al. PaxDb, a database of protein abundance averages across all three domains of life. Mol Cell Proteomics. Aug. 2012; 11(8): 492-500.
Wennier, S.T. et al. Bugs and drugs: oncolytic virotherapy in combination with chemotherapy. Curr. Pharm. Biotechnol. 2012;13:1817-1833.
Wennier, S.T. et al. Myxoma virus sensitizes cancer cells to gemcitabine and is an effective oncolytic virotherapeutic in models of disseminated pancreatic cancer. Mol Ther. Apr. 2012;20(4):759-68. doi: 10.1038/mt.2011.293. Epub Jan. 10, 2012. PMID: 22233582; PMCID: PMC3321583.
Werden, S.J. & Mcfadden, G. Pharmacological manipulation of the akt signaling pathway regulates myxoma virus replication and tropism in human cancer cells. J Virol.Apr. 2010; 84(7): 3287-3302.

(56) References Cited

OTHER PUBLICATIONS

Werden, S.J. et al. The myxoma virus m-t5 ankyrin repeat host range protein is a novel adaptor that coordinately links the cellular signaling pathways mediated by Akt and Skp1 in virus-infected cells. J Virol. Dec. 2009; 83(23): 12068-12083.
Wiebe, M.S. & Traktman, P. Poxviral B1 kinase overcomes barrier to autointegration factor, a host defense against virus replication. Cell Host Microbe. May 17, 2007;1(3):187-97. doi: 10.1016/j.chom.2007.03.007.
Wilke, C.M. et al. Antigen-presenting cell (APC) subsets in ovarian cancer. Int. Rev. Immunol. 2011;30:120-126.
Woller, N. et al. Oncolytic viruses as anticancer vaccines. Front. Oncol. 2014;4:188.
Wu, J.J., et al. Inhibition of cGAS DNA Sensing by a Herpesvirus Virion Protein. Cell host & microbe 2015, 18(3): 333-344.
Yu, H. et al. STATs in cancer inflammation and immunity: a leading role for STAT3. Nat Rev Cancer. Nov. 2009;9 (11):798-809. doi: 10.1038/nrc2734.
Zhang, L. et al. Intratumoral T cells, recurrence, and survival in epithelial ovarian cancer. N. Engl. J. Med. 2003;348:203-213.
Zhang, N. The C. elegans Excretory Canal as a Model for Intracellular Lumen Morphogenesis and In Vivo Polarized Membrane Biogenesis in a Single Cell: labeling by GFP-fusions, RNAi Interaction Screen and Imaging. J Vis Exp. 2017; (128): 56101.
Zhang, Z. et al. The helicase DDX41 senses intracellular DNA mediated by the adaptor STING in dendritic cells. Nature immunology 2011, 12(10): 959-965.
Curiel, T.J. et al. Blockade of B7-H1 improves myeloid dendritic cell-mediated antitumor immunity. Nat Med. May 2003;9(5):562-7. doi: 10.1038/nm863. Epub Apr. 21, 2003. PMID: 12704383.
Gentili, M. et al. Transmission of innate immune signaling by packaging of cGAMP in viral particles. Science (New York, NY) 2015, 349(6253): 1232-1236.
Jeklova, E. et al. Characterisation of immunosuppression in rabbits after infection with myxoma virus. Veterinary microbiology 2008, 129(1-2): 117-130.
Kerr, P.J. & Best, S.M. Myxoma virus in rabbits. Rev Sci Tech. Apr. 1998;17(1):256-68. doi: 10.20506/rst.17.1.1081.
Liddy, N. et al. Monoclonal TCR-redirected tumor cell killing. Nature Med. 18:980-7 (2012).
Loercher, A.E. et al. Identification of an IL-10-producing HLA-DR-negative monocyte subset in the malignant ascites of patients with ovarian carcinoma that inhibits cytokine protein expression and proliferation of autologous T cells. J. Immunol. 1999;163:6251-6260.
Narumi S. et al. SAMD9 mutations cause a novel multisystem disorder, MIRAGE syndrome, and are associated with loss of chromosome 7. Nature genetics 2016, 48(7): 792-797.
Nitta, T. et al. Preliminary trial of specific targeting therapy against malignant glioma. Lancet, 355: 368-371, 1990.
Perkus, M.E. et al. Vaccinia virus host range genes. Virology. Nov. 1990;179(1):276-86. doi: 10.1016/0042-6822(90)90296-4.
Petrovsky, N. & Aguilar J.C. Vaccine adjuvants: current state and future trends. Immunol Cell Biol. Oct. 2004;82 (5):488-96. doi: 10.1111/j.0818-9641.2004.01272.x. PMID: 15479434.
Scherer, O. et al. A procedure for efficient non-viral siRNA transfection of primary human monocytes using nucleofection. Journal of immunological methods 2015, 422: 118-124.
Schnoor, M. et al. Efficient non-viral transfection of THP-1 cells. Journal of immunological methods 2009, 344(2): 109-115.
Trzeciak-Ryczek, A. et al. Expression of IL-1Ra, IL-6, IL-8, IL-18, TNF-alpha and IFN-gamma genes in peripheral blood leukocytes of rabbits infected with RHDV (Rabbit Haemorrhagic Disease Virus). Developmental and comparative immunology 2017, 76: 310-315.
Van Der Woude, L.L. et al., Migrating into the Tumor: a Roadmap for T Cells2017 Trends in Cancer. Trends Cancer. Nov. 2017;3(11):797-808. doi: 10.1016/j.trecan.2017.09.006. Epub Nov. 6, 2017.

Zhang, L-K, et al. Identification of host proteins involved in Japanese encephalitis virus infection by quantitative proteomics analysis. J Proteome Res. Jun. 7, 2013;12(6):2666-78. doi: 10.1021/pr400011k. Epub May 21, 2013.
Cho et al, Anticancer Research vol. 33, p. 1317, 2013.
Paijo, J. et al. cGAMP Quantification in Virus-Infected Human Monocyte-Derived Cells by HPLC-Coupled Tandem Mass Spectrometry. Methods Mol Biol.2017:1656:153-166. doi: 10. 1007/978-1-4939-7237-1_9.
Nair, R.R et al. Role of STAT3 in transformation and drug resistance in CML. Front. Oncol. 2012;2:30.
Nejad, E.B. et al. Tumor eradication by cisplatin is sustained by CD80/86-mediated costimulation of CD8+ T cells. Cancer Res. 2016;76:6017-6029.
Nounamo, B. et al. Myxoma Virus Optimizes Cisplatin for the Treatment of Ovarian Cancer In Vitro and in a Syngeneic Murine Dissemination Model. Mol Ther Oncolytics. Aug. 9, 2017;6:90-99. doi: 10.1016/j.omto.2017.08.002. PMID: 28875159; PMCID: PMC5573804.
Oguiura, N. et al. Detection of a protein encoded by the vaccinia virus C7L open reading frame and study of its effect on virus multiplication in different cell lines. The Journal of general virology 1993, 74 ( Pt 7): 1409-1413.
Ohmichi, T. et al. Efficient bacterial transcription of DNA nanocircle vectors with optimized single-stranded promoters. Proceedings of the National Academy of Sciences 2002, 99, 54-59.
Ossovskaya, V. et al. Upregulation of Poly (ADP-Ribose) Polymerase-1 (PARP1) in Triple-Negative Breast Cancer and Other Primary Human Tumor Types. Genes Cancer. Aug. 2010; 1(8):812-21.
Ozols, R.F. Challenges for chemotherapy in ovarian cancer. Ann. Oncol. 2006;17(Suppl 5):v181-v187.
Pagano, J.M. et al. Quantitative approaches to monitor protein-nucleic acid interactions using fluorescent probes. RNA. Jan. 2011;17(1):14-20. doi: 10.1261/rna.2428111. Epub Nov. 22, 2010.
Paijo, J. et al. cGAS Senses Human Cytomegalovirus and Induces Type I Interferon Responses in Human Monocyte-Derived Cells. PLoS pathogens 2016, 12(4): e1005546.
Pandha, H.S. et al. Synergistic effects of oncolytic reovirus and cisplatin chemotherapy in murine malignant melanoma. Clin. Cancer Res. 2009;15:6158-6166.
Pennington, T.H. Vaccinia virus polypeptide synthesis: sequential appearance and stability of pre- and post-replicative polypeptides. J Gen Virol. Dec. 1974;25(3):433-44. doi: 10.1099/0022-1317-25-3-433.
Peters, N.E. et al. A mechanism for the inhibition of DNA-PK-mediated DNA sensing by a virus. PLoS pathogens 2013, 9(10): e1003649.
Preston, C.C. et al. The ratios of CD8+ T cells to CD4+CD25+FOXP3+ and FOXP3− T cells correlate with poor clinical outcome in human serous ovarian cancer. PLoS One. Nov. 14, 2013;8(11):e80063. doi: 10.1371/journal.pone.0080063. PMID: 24244610; PMCID: PMC3828213.
Rahman, M.M. et al. Myxoma virus protein M029 is a dual function immunomodulator that inhibits PKR and also conscripts RHA/DHX9 to promote expanded host tropism and viral replication. PLoS pathogens 2013, 9(7): e1003465.
Ran, F.A. et al. Genome engineering using the CRISPR-Cas9 system. Nature protocols 2013, 8(11): 2281-2308.
Ribas, A. & Wolchok, J.D. Cancer immunotherapy using checkpoint blockade. Science. Science. Mar. 23, 2018;359 (6382):1350-1355. doi: 10.1126/science.aar4060. Epub Mar. 22, 2018.
Roby, K.F. et al. Development of a syngeneic mouse model for events related to ovarian cancer. Carcinogenesis. 2000;21:585-591.
Rochester, S.C. & Traktman, P. Characterization of the single-stranded DNA binding protein encoded by the vaccinia virus 13 gene. J Virol. Apr. 1998; 72(4): 2917-2926.
Rosenberg, S.A. et al. Adoptive cell transfer: a clinical path to effective cancer immunotherapy. Nat. Rev. Cancer 8 (4): 299-308 (2008).
Satheshkumar, P.S. et al. Inhibition of the ubiquitin-proteasome system prevents vaccinia virus DNA replication and expression of intermediate and late genes. J Virol. Mar. 2009;83(6):2469-79.

(56) References Cited

OTHER PUBLICATIONS

Sayers, S. et al. Vaxjo: a web-based vaccine adjuvant database and its application for analysis of vaccine adjuvants and their uses in vaccine development. J Biomed Biotechnol. 2012;2012:831486. doi: 10.1155/2012/831486. Epub Mar. 13, 2012. PMID: 22505817; PMCID: PMC3312338.

Schmidt, F.I. et al. Vaccinia virus entry is followed by core activation and proteasome-mediated release of the immunomodulatory effector VH1 from lateral bodies. Cell reports 2013, 4(3): 464-476.

Schust, J. et al. Stattic: a small-molecule inhibitor of STAT3 activation and dimerization. Chem. Biol. 2006; 13:1235-1242.

Schwartz, J.R. et al. Germline SAMD9 mutation in siblings with monosomy 7 and myelodysplastic syndrome. Leukemia. Aug. 2017;31(8):1827-1830. doi: 10.1038/leu.2017.142. Epub May 10, 2017.

Senkevich, T.G. et al. Identification of Vaccinia Virus Replisome and Transcriptome Proteins by Isolation of Proteins on Nascent DNA Coupled with Mass Spectrometry. J Virol. Sep. 12, 2017;91(19):e01015-17. doi: 10.1128/JVI.01015-17. Print Oct. 1, 2017.

Seo, G.J. et al. Akt Kinase-Mediated Checkpoint of cGAS DNA Sensing Pathway. Cell reports 2015, 13(2): 440-449.

Shchelkunov, S.N. An increasing danger of zoonotic orthopoxvirus infections. PLoS pathogens 2013,9(12): e1003756.

Shen, Y.J. et al. Genome-derived cytosolic DNA mediates type I interferon-dependent rejection of B cell lymphoma cells. Cell reports 2015, 11(3): 460-473.

Simpson, G.R. et al. Cancer immunotherapy via combining oncolytic virotherapy with chemotherapy: recent advances. Oncolytic Virother. 2016;5:1-13.

Sivan, G. Identification of Restriction Factors by Human Genome-Wide RNA Interference Screening of Viral Host Range Mutants Exemplified by Discovery of SAMD9 and WDR6 as Inhibitors of the Vaccinia Virus K1L-C7L-Mutant. mBio 2015, 6(4): e01122.

Spiesschaert, B. et al. The current status and future directions of myxoma virus, a master in immune evasion. Veterinary research 2011, 42: 76.

Clinical Trials Arena. Spotlight on IDO Inhibitors with crucial clinical trial readout on the horizon. Mar. 2, 2018. <https://clinicaltrialsarena.com/comment/spotlight-ido-inhibitors-crucial-clinical-trial-readout-horizon/?cf-view&cf-closed>.

Springer, Y.P. et al. Novel Orthopoxvirus Infection in an Alaska Resident. Clin Infect Dis. Jun. 15, 2017; 64(12): 1737-1741.

Suen, W.W. et al. Tissue-specific transcription profile of cytokine and chemokine genes associated with flavivirus control and non-lethal neuropathogenesis in rabbits. Virology 2016, 494: 1-14.

Sun, L. Cyclic GMP-AMP synthase is a cytosolic DNA sensor that activates the type I interferon pathway. Science (New York, NY) 2013, 339(6121): 786-791.

Tan, M.C. Disruption of CCR5-dependent homing of regulatory T cells inhibits tumor growth in a murine model of pancreatic cancer. J. Immunol. 2009;182:1746-1755.

Taylor, R.T. et al. TRIM79alpha, an interferon-stimulated gene product, restricts tick-borne encephalitis virus replication by degrading the viral RNA polymerase. Cell Host Microbe. Sep. 15, 2011; 10(3): 185-196. doi:10.1016/j.chom.2011.08.004.

Thorne, S.H. et al. Targeting localized immune suppression within the tumor through repeat cycles of immune cell-oncolytic virus combination therapy. Mol. Ther. 2010;18:1698-1705.

Tolonen, N. et al. Vaccinia virus DNA replication occurs in endoplasmic reticulum-enclosed cytoplasmic mini-nuclei. Mol Biol Cell. Jul. 2001; 12(7): 2031-2046.

Tong, J.G. et al. Evidence for differential viral oncolytic efficacy in an in vitro model of epithelial ovarian cancer metastasis. Mol. Ther. Oncolytics. 2015;2:15013.

Topaz, O. et al. A deleterious mutation in SAMD9 causes normophosphatemic familial tumoral calcinosis. Am J Hum Genet. Oct. 2006;79(4):759-64. doi: 10.1086/508069. Epub Aug. 24, 2006.

Tseng, C.W. et al. Pretreatment with cisplatin enhances E7-specific CD8+ T-cell-mediated antitumor immunity induced by DNA vaccination. Clin. Cancer Res. 2008; 14:3185-3192.

UniProt Q5K651. SAMD9_Human, Nov. 7, 2018 [online]. Retrieved Jan. 29, 2020]. <URL:https://www/uniprot.org/uniprot/Q5K651.txt?version=125>.

Unterholzner, L. et al. IFI16 is an innate immune sensor for intracellular DNA. Nature immunology 2010, 11(11): 997-1004.

Van Den Boogaard, J. et al. New Drugs against Tuberculosis: Problems, Progress, and Evaluation of Agents in Clinical Development. Antimicrobial Agents and Chemotherapy 2009, 53, 849-862.

Villa, N.Y. et al. Myxoma and vaccinia viruses exploit different mechanisms to enter and infect human cancer cells. Virology 2010, 401(2): 266-279.

Walton, J. et al. CRISPR/Cas9-Mediated Trp53 and Brca2 Knockout to Generate Improved Murine Models of Ovarian High-Grade Serous Carcinoma. Cancer Res. Oct. 15, 2016;76(20):6118-6129. doi: 10.1158/0008-5472.CAN-16-1272. Epub Aug. 16, 2016. PMID: 27530326; PMCID: PMC5802386.

Wang, F. et al. Disruption of Erk-dependent type I interferon induction breaks the myxoma virus species barrier. Nature immunology 2004, 5(12): 1266-1274.

Wang, F. et al. Induction of alpha/beta interferon by myxoma virus is selectively abrogated when primary mouse embryo fibroblasts become immortalized. J. Virol. 2009;83:5928-5932.

"3rd Global GLC Meeting Report 2012. Session I—Report from the gGLC Secretariat," World Health Organization: Geneva, Switzerland, 2012.

Albrecht, L.V. et al. GSK3- and PRMT-1-dependent modifications of desmoplakin control desmoplakin-cytoskeleton dynamics. The Journal of cell biology 2015, 208(5): 597-612.

Almine, J.F. et al. IFI16 and cGAS cooperate in theactivation of STING during DNA sensing in human keratinocytes. Nature communications 2017, 8:14392.

Ansari, M.A. et al. Herpesvirus Genome Recognition Induced Acetylation of Nuclear IFI16 Is Essential for Its Cytoplasmic Translocation, Inflammasome and IFN-beta Responses. PLoS pathogens 2015, 11(7): e1005019.

Arulanandam, R. et al. Microtubule disruption synergizes with oncolytic virotherapy by inhibiting interferon translation and potentiating bystander killing. Nat. Commun. 2015;6:6410.

Bartee, E. & and Mcfadden, G. Human cancer cells have specifically lost the ability to induce the synergistic state caused by tumor necrosis factor plus interferon-beta. Cytokine. 2009;47:199-205.

Bartee, E. et al. Myxoma virus induces ligand independent extrinsic apoptosis in human myeloma cells. Clin. Lymphoma Myeloma Leuk. 2016;16:203-212.

Bartee, E. et al. The addition of tumor necrosis factor plus beta interferon induces a novel synergistic antiviral state against poxviruses in primary human fibroblasts. J. Virol. 2009; 83:498-511.

Bauer, D.E. et al. Generation of genomic deletions in mammalian cell lines via CRISPR/Cas9. Journal of visualized experiments : JoVE 2015(95): e52118.

Becker, K.P. & Hannun, Y.A. cPKC-dependent sequestration of membrane-recycling components in a subset of recycling endosomes. The Journal of biological chemistry 2003, 278(52): 52747-52754.

Best, S.M. & Kerr, P.J. Coevolution of host and virus: the pathogenesis of virulent and attenuated strains of myxoma virus in resistant and susceptible European rabbits. Virology 2000, 267(1): 36-48.

Best, S.M. et al. Coevolution of host and virus: cellular localization of virus in myxoma virus infection of resistant and susceptible European rabbits. Virology 2000, 277(1): 76-91.

Bilsland, A.E. et al. Virotherapy: cancer gene therapy at last? Version 1. F1000Res. 2016; 5: F1000 Faculty Rev-2105.

Braun, C. et al. Genetic Variability of Myxoma Virus Genomes. J Virol. Feb. 15, 2017; 91(4): e01570-16.

Buonocore, F. et al. Somatic mutations and progressive monosomy modify SAMD9-related phenotypes in humans. The Journal of clinical investigation 2017, 127(5): 1700-1713.

Cameron, C. et al. The complete DNA sequence of myxoma virus. Virology. Nov. 25, 1999;264(2):298-318. doi: 10.1006/viro.1999.0001.

(56) References Cited

OTHER PUBLICATIONS

Campbell, E.A. et al. Structural Mechanism for Rifampicin Inhibition of Bacterial RNA Polymerase. Cell 2001, 104, 901-912.
Cancer Facts & Figures. 2018. The American Cancer Society. https://cancer.org/research/cancer-facts-statistics/all-cancer-facts-figures/cancer-facts-figures-2018.html.
Cannon, M.J. et al. Signaling circuits and regulation of immune suppression by ovarian tumor-associated macrophages. Vaccines (Basel) 2015;3:448-466.
Casey, A.E. Studies in the Blood Cytology of the Rabbit : VI Blood Cell Relationships in Groups of Normal Rabbits With Respect to Time. J Exp Med. Apr. 30, 1931;53(5):695-714. doi: 10.1084/jem.53.5.695.
Chan, W.M. & Mcfadden, G. Oncolytic Poxviruses. Annual review of virology 2014, 1(1): 119-141.
Chan, W.M. et al. Myxoma and vaccinia viruses bind differentially to human leukocytes. J. Virol. 2013;87:4445-4460.
Chan, W.M. et al. Oncolytic myxoma virus: the path to clinic. Vaccine 2013,31(39): 4252-4258.
Chang, C-L, et al. Dose-dense chemotherapy improves mechanisms of antitumor immune response. Cancer Res. 2013;73:119-127.
Chefetz, I. et al. Normophosphatemic familial tumoral calcinosis is caused by deleterious mutations in SAMD9, encoding a TNF-alpha responsive protein. The Journal of investigative dermatology 2008, 128(6): 1423-1429.
Chen, Q. et al. Regulation and function of the cGAS-STING pathway of cytosolic DNA sensing. Nature immunology 2016, 17(10): 1142-1149.
Clift, D. et al. A Method for the Acute and Rapid Degradation of Endogenous Proteins. Cell 2017, 171(7): 1692-1706 e1618.
Cong, L. et al. Multiplex genome engineering using CRISPR/Cas systems. Science (New York, NY) 2013, 339(6121): 819-823.
Correa, R.J. et al. Myxoma virus-mediated oncolysis of ascites-derived human ovarian cancer cells and spheroids is impacted by differential AKT activity. Gynecol. Oncol. 2012; 125:441-450.
Dasari S. & Tchounwou, P.B. Cisplatin in cancer therapy: molecular mechanisms of action. Eur. J. Pharmacol. 2014;740:364-378.
Dell'Oste, V. et al. Innate nuclear sensor IFI16 translocates into the cytoplasm during the early stage of in vitro human cytomegalovirus infection and is entrapped in the egressing virions during the late stage. Journal of virology 2014, 88(12): 6970-6982.
Dijkgraaf, E.M. et al. Chemotherapy alters monocyte differentiation to favor generation of cancer-supporting M2 macrophages in the tumor microenvironment. Cancer Res. 2013;73:2480-2492.
Ding, S. et al. STAG2 deficiency induces interferon responses via cGAS-STING pathway and restricts virus infection. Nature communications 2018, 9(1): 1485.
Dunlap, K.M. et al. Myxoma virus attenuates expression of activating transcription factor 4 (ATF4) which has implications for the treatment of proteasome inhibitor-resistant multiple myeloma. Oncolytic Virother. 2015;4:1-11.
Dunn, G.P. et al. The immunobiology of cancer immunosurveillance and immunoediting. Immunity. Aug. 2004;21 (2):137-48. doi: 10.1016/j.immuni.2004.07.017.
Esteves, P.J. et al. The wide utility of rabbits as models of human diseases. Experimental & molecular medicine 2018, 50(5): 66.
Ferguson, B.J. et al. DNA-PK is a DNA sensor for IRF-3-dependent innate immunity. eLife 2012, 1: e00047.
Fukuhara, H. et al. Oncolytic virus therapy: a new era of cancer treatment at dawn. Cancer Sci. 2016; 107:1373-1379.
Garrod, D & Chidgey, M. Desmosome structure, composition and function. Biochimica et biophysica acta 2008, 1778(3): 572-587.
Georgana, I. et al. Virulent poxviruses inhibit DNA sensing by preventing STING activation. J Virol. Apr. 27, 2018;92 (10):e02145-17. doi: 10.1128/JVI.02145-17. Print May 15, 2018.
Global Tuberculosis Report 2017, World Health Organization: Geneva, Switzerland, 2017.
Godsel, L.M. et al. Desmoplakin assembly dynamics in four dimensions: multiple phases differentially regulated by intermediate filaments and actin. The Journal of cell biology 2005, 171(6): 1045-1059.
Goyne, H.E. & Cannon, M.J. Dendritic cell vaccination, immune regulation, and clinical outcomes in ovarian cancer. Front. Immunol. 2013;4:382.
Goyne, H.E. et al. Ovarian tumor ascites CD14+ cells suppress dendritic cell-activated CD4+ T-cell responses through IL-10 secretion and indoleamine 2,3-dioxygenase. J. Immunother. 2014; 37: 163-169.
Grupp, S.A. et al. Chimeric Antigen Receptor-Modified T Cells for Acute Lymphoid Leukemia. New England J. Med. 368:1509-18, (2013).
Gujar, S.A. Gemcitabine enhances the efficacy of reovirus-based oncotherapy through anti-tumour immunological mechanisms. Br. J. Cancer. 2014;110:83-93.
Hershkovitz, D. et al. Functional characterization of SAMD9, a protein deficient in normophosphatemic familial tumoral calcinosis. The Journal of investigative dermatology 2011, 131(3): 662-669.
Hobbs, R.P. & Green, K.J. Desmoplakin regulates desmosome hyperadhesion. The Journal of investigative dermatology 2012, 132(2): 482-485.
Horan, K.A. et al. Proteasomal degradation of herpes simplex virus capsids in macrophages releases DNA to the cytosol for recognition by DNA sensors. Journal of immunology 2013, 190(5): 2311-2319.
Centers for Disease Control and Prevention. Tuberculosis (TB) <http://.cdc.gov/tb/> (accessed January 14th).

\* cited by examiner

Deletion of SAMD9 rescued M062R-null MYXV infection to WT levels.

Viral yield at Log(pfu/mL) vs Time Points (hrs)

- M062R-null MYXV_SAMD9+/+ cells
- WT MYXV_SAMD9-/- cells
- M062R-null MYXV_SAMD9-/- cells FIG. 6A
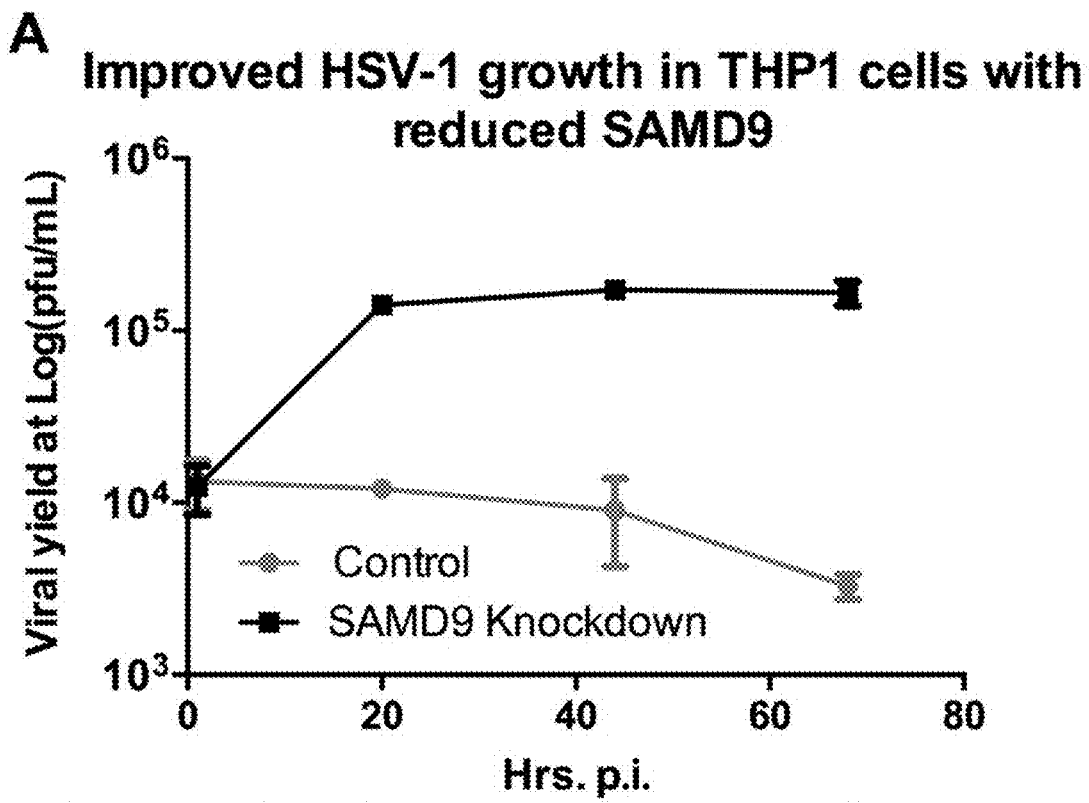
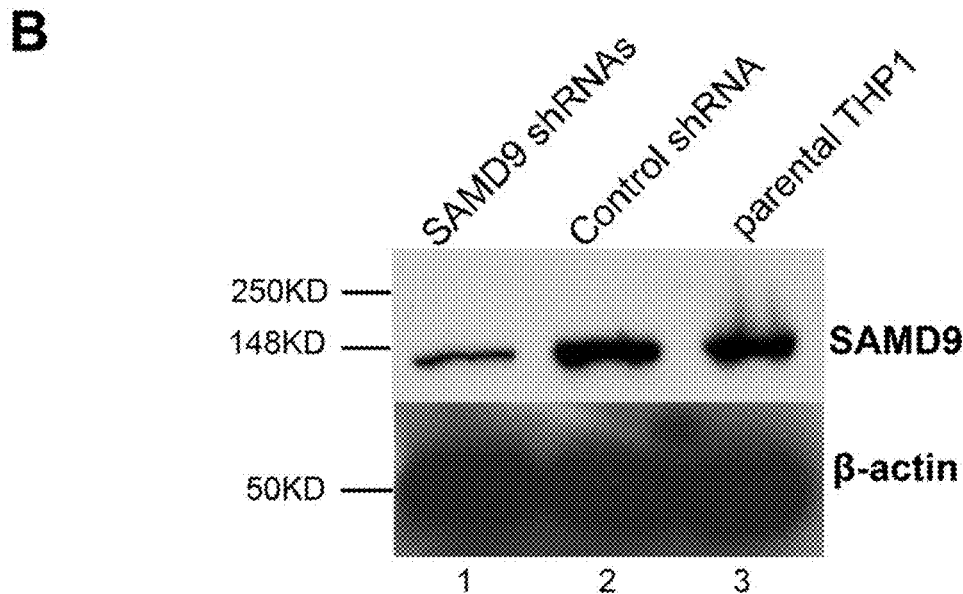
FIG. 6B

CELLS FOR THE PRODUCTION OF VIRUSES AND METHODS OF USING THE SAME

CROSS-REFERENCE TO RELATED APPLICATIONS

This application is a national stage filing under 35 U.S.C. 371 of International Application No. PCT/US2019/062470, filed Nov. 20, 2019, which claims benefit to U.S. Provisional Application No. 62/769,834 filed on Nov. 20, 2018, the contents of all of which are incorporated herein by reference in their entireties.

STATEMENT REGARDING FEDERALLY SPONSORED RESEARCH

This invention was made with government support under R01 AI139106 and K22-AI099184 awarded by the National Institutes of Health. The government has certain rights in the invention.

SEQUENCE LISTING

A Sequence Listing accompanies this application and is submitted as a ASCII text file of the sequence listing named "2019-11-18_169852_00056_ST25" which is 25688 kb in size and was created on May 20, 2021. The sequence listing is electronically submitted via EFS-Web with the application and is incorporated herein by reference in its entirety.

INTRODUCTION

Viruses are used in biotechnology applications as research tools, diagnostic agents, and therapeutic agents. As therapeutic agents, viruses may be used as vaccines, vectors for gene therapy, anti-cancer oncolytic agents, or immunotherapeutics. A viruses' usefulness in these applications, however, is partly dependent on having efficient means of producing the virus at titers that are sufficient for a particular application. There thus remains a need in the art for new viral production methods that improve viral titer.

As an exemplary virus with therapeutic potential, myxoma virus (MYXV) is a poxvirus with a narrow host range in nature, infecting only rabbits. However, wild-type MYXV and many mutant MYXVs possess oncolytic potential and have recently been shown to be an excellent immunotherapeutic agent. Their safety feature, outstanding therapeutic potential shown in many cancer types, and versatility of application approaches make them attractive for human disease therapy. To generate large quantities of MYXV has been challenging. It is largely because MYXV relies on cell-to-cell contact for the transmission of the progeny viruses. Thus conventional suspension culture cannot not provide optimal yield for MYXV production. For the same reason, monolayer cell lines that can support optimal production of other viruses supply limited viral production. Thus improving MYXV yield is a critical task for future therapeutic applications using MYXV. The present invention, for example, defines a way to significantly improve the yield of replicating MYXV in an FDA approved human cell line, A549, permitting a significantly improved viral production.

In addition to replicating MYXV, the engineered cell line permits production of a non-replicating MYXV that has a promising therapeutic potential as well. We previously found that a mutant MYXV deleted for the viral immuno-regulatory gene, M062R (M062R-null MYXV) had a beneficial therapeutic effect despite an abortive infection. In human primary ovarian cancer cells M062R-null MYXV induces a potent inflammatory response that includes type I interferon (IFN-I) responses. Moreover, it effectively improved survival when it is administrated after cisplatin, the first line chemotherapy for ovarian cancer.

Although M062R-null MYXV shows therapeutic promise, it is difficult to produce in high titers that will be sufficient to conduct, for example, clinical trials because the virus produces an abortive infection. We sought to develop new compositions and methods that could be used to improve the titer of both replicating and non-replicating MYXV (e.g., M062R-null MYXV) as well as other viruses. Such compositions and methods should help realize the potential of viruses as important research tools, diagnostic agents, and therapeutic agents.

SUMMARY

In one aspect of the present invention, cells are provided. The cells may be modified to eliminate or reduce as compared to a control cell the activity or expression of a Sterile α motif-domain containing protein 9 (SAMD9) polypeptide.

In another aspect, the present invention relates to methods of producing a virus. The methods may include introducing the virus into any one of the cells described herein. Optionally, the methods may also further include purifying the virus from the cell.

BRIEF DESCRIPTION OF DRAWINGS

FIG. 1 shows a sequence alignment. The sequence alignment was created using a sequencing result from a representative clone (E1) of SAMD9-null cells that was engineered using CRISPR/CAS9 technology in human cell line A549 cells (ATCC® CCL-185™). SAMI) 9 mRNA: numbering is according to NCBI Reference Sequence of NM_001193307.1. SAMD9 CDS was obtained from NCBI CCDS34680.1. The reference polynucleotide sequence displayed is from NCBI Reference Sequence NM_001193307.1 (SEQ ID NO: 6). The reference amino acid (AA) sequence shown (SEQ ID NO: 7) is the amino acid sequence translated from SAMD) 9 mRNA. Sequencing result: The genomic DNA sequence of SAMD9 from a representative clone (E1) of SAMD9-null cells (SEQ ID NO: 8). Amino acid (AA) sequence: The amino acid sequence of SAMD9 that was converted from the sequencing result (SEQ ID NO: 9). The premature stop codon introduced by the CRISPR/CAS9 led to a production of truncated protein of 212 aa. The same deletion was found in HeLa SAMD9-null cell clones, e.g., B3.

FIG. 3 shows deleting SAMD9 from A549 cells restored M062R-null MYXV infection comparable to WT MYXV. A low multiplicity of infection (MOI) at 0.1 for either M062R-null or WT MYXV was used to infect either A549 SAMD9+/+ (parental) or SAMD9−/− (SAMD9-null) cells. At given time points, cell lysates were harvested for titration on BSC40 cells. Statistical significance was determined by multiple t tests (Holm-Sidak method) with α=5.000% defined as being statistically significant ( p<0.001, and * p<0.0001).

(FIG. 5A) Inhibition of RNA synthesis after 1 hr post infection did not affect the difference in viral input. Actinomycin D (ActD) is an inhibitor for RNA synthesis. Although treating cells at 2 µg/ml during infection did reduce the overall luciferase activity compared with untreated corresponding infection, Act D treatment did not eliminate the elevated luciferase activity resulting from infecting SAMD9-null cells. (FIG. 5B) Inhibition of viral DNA replication did not reduce the improved viral infection in SAMD9-null cells. Cytosine arabinoside (AraC) is a specific inhibitor of poxvirus DNA replication. Pre-treating cells 30 minutes before infection followed by its presence during and after infection at 50 µM did not affect luciferase activity emitted from infection in both cell lines. AraC treatment at this dose inhibits post-replicative gene expression and thus reduce overall viral yield. (FIG. 5C) Inhibition of virion uncoating did not reduce the improvement in viral infection in SAMD9-null cells. MG132 is known to inhibit poxvirus virion uncoating, which occurs after virion entry. We used a dose of 10 µM to pretreat cells 30 minutes before infection, and during and throughout the rest course of infection. We found that inhibition of virion uncoating also did not affect improved infection occurred in SAMD9-null cells. (FIG. 5D) SAMD9 deletion leads to significant improvement of MYXV infection in A549 cells. A separate group of cells were infected with the same amount of virus as in A, B, and C without drug treatment and at 24 h post-infection viral yield was evaluated by titration as previously described. Using multiple t tests we found in SAMD9-null cell WT MYXV infection can be significantly improved by a log.

FIGS. 6A-6B show knocking-down SAMD9 expression in another human cell line, THP1, leads to dramatic increase of HSV-1 infection. (FIG. 6A) Knocking down SAMD9 improved HSV-1 infection. HSV-1 infection was conducted in PMA-differentiated THP1 cells (ATCC© TIB-202™) and at given time points cell lysates were collected for titration on RS cells as previously described.[8] (FIG. 6B) Characterization of SAMD9 knockdown THP1 cells. The SAMD9 knockdown cells were engineered using lentivirus expressing shRNAs targeting SAMD9 mRNA and the control cells were engineered using lentivirus expressing control shRNAs; to engineer these cell lines we utilized a method similar to what has been reported.[2] In the western blot, a reduced SAMD9 protein level is seen in cells stably expressing SAMD9 targeting shRNAs, while introduction of non-targeting shRNAs (control) did not affect SAMD9 expression.

DETAILED DESCRIPTION

Figure 2:
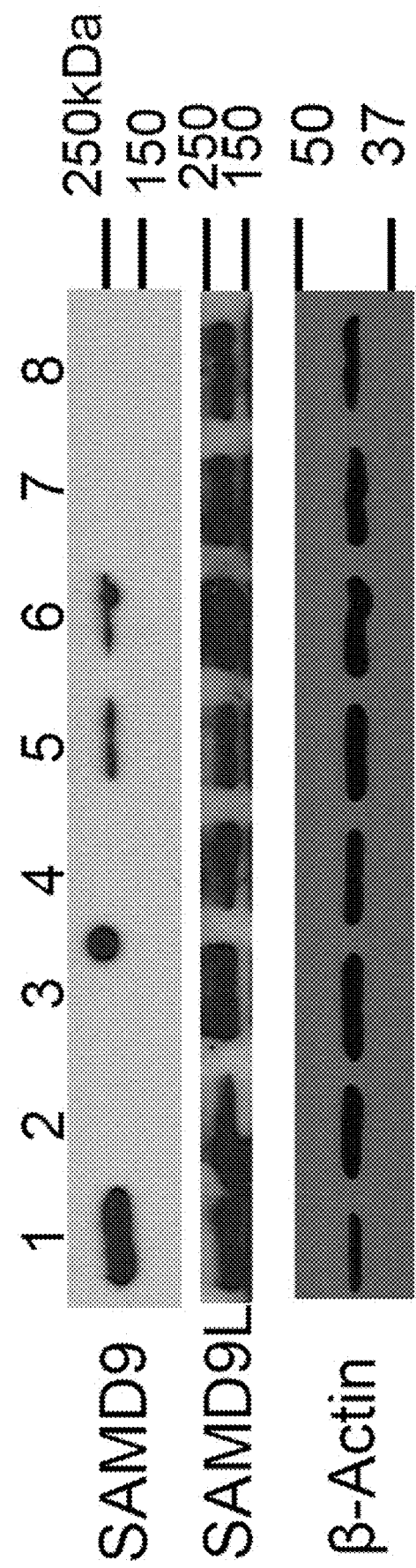
FIG. 2 shows a western blot analysis of single cell clones that were engineered to delete SAMD9 expression. Normal expression of a neighboring gene SAMD9L is also shown along with internal loading control using β-actin. Lane 1: A549 cells expressing normal level of SAMD9; lane 2-8 are clone C1, E1, F1, G1, A2, B2, and C2, respectively.
Figure 4:
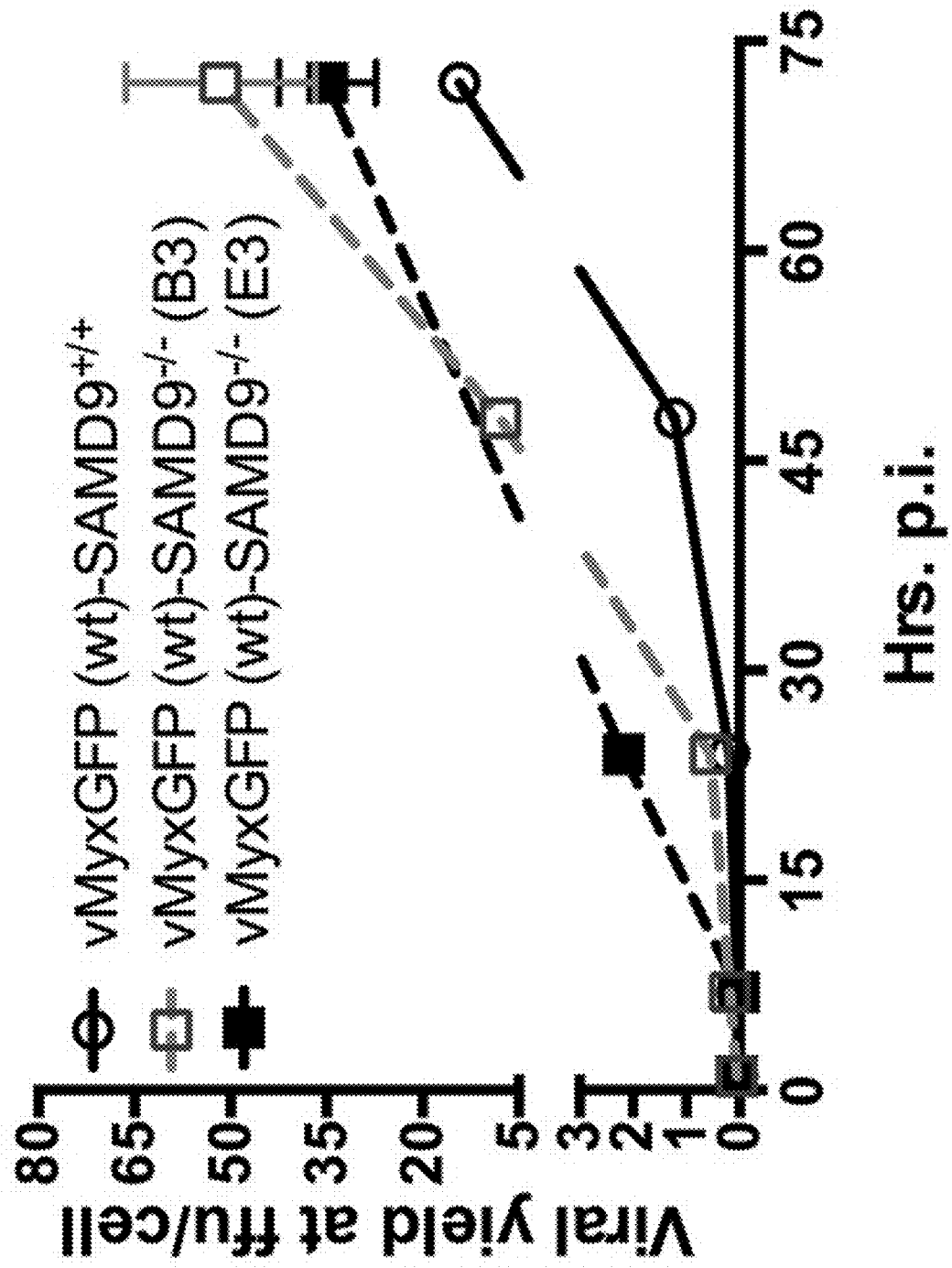
FIG. 4 shows single cell clones of HeLa cells with SAMD9 deleted improved WT MYXV viral yield. In engineered SAMD9-null HeLa cell clones, WT MYXV infection is significantly improved. Using the multiple t test, we found at each given time point (7, 24, 48, and 72 hrs) other than 1 hr input both SAMD9-null cell lines support significantly increased viral yield (p<0.05).
Figures 5A, 5B, 5C, 5D:
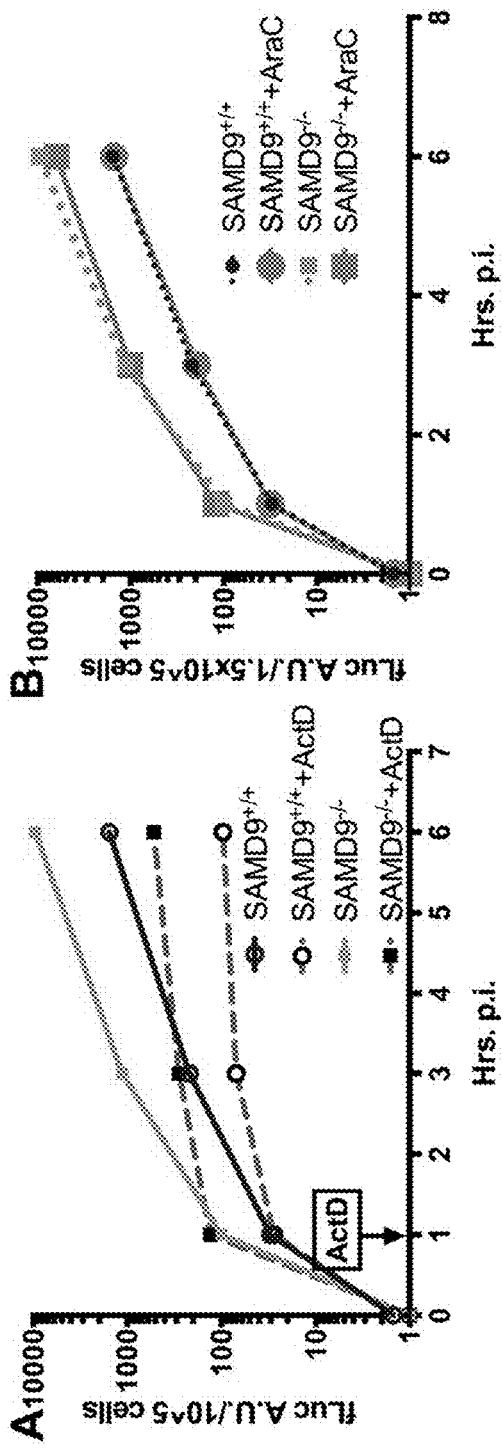
FIGS. 5A-5D show SAMD9-null A549 cells permit significantly increased MYXV infection. We used a well-characterized entry assay[7] to examine the mechanism of SAMD9-null A549 cells on how it can achieve such dramatic increase in MYXV viral infection. The WT MYXV used in this assay expressing firefly luciferase immediately after entering the cells and by examining the luciferase activity using an appropriate substrate we can measure and quantify the virus input. This is a very sensitive assay. We included many controls so that we can examine the process of infection that lead to an improved viral yield.

Here, in the non-limiting Examples, the present inventors have created cells and methods that improve the production of myxoma viruses, including wild-type replication-competent myxoma viruses and replication-defective mutant myxoma viruses. In addition to myxoma viruses, the present inventors show that the disclosed cells and methods also improve the production of other viruses such as, without limitation, herpes simplex viruses, poxviruses, reoviruses and rota viruses.

Cells

In one aspect of the present invention, cells are provided. The cells may be modified to eliminate or reduce as compared to a control cell the activity or expression of a Sterile α motif-domain containing protein 9 (SAMD9) polypeptide.

As used herein, the terms "polypeptide" or "protein" or "peptide" may be used interchangeably to refer to a polymer of amino acids. A "polypeptide" as contemplated herein typically comprises a polymer of naturally occurring amino acids (e.g., alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine).

Sterile α motif-domain containing protein 9 (SAMD9) polypeptides play critical roles in human health and may play a role in the inflammatory response to tissue injury and the control of extra-osseous calcification. The present inventors previously found that SAMD9 has antiviral function against poxviruses and poxviruses have evolved many viral proteins to inhibit SAMD9 function.[1,2]

SEQ ID NO: 1 is an exemplary SAMD9 polypeptide from humans that may be used as a reference sequence. SAMD9 polypeptides from other species may also be used as reference sequences and can be found by a person of ordinary skill in the art by using SEQ ID NO: 1 to identify similar sequences from other species in databases such as at the National Center for Biotechnology Information (NCBI). The polypeptides disclosed herein (i.e., SAMD9 polypeptides and M062R polypeptides) may include "homologs" of the polypeptides disclosed herein. A "homolog" may be a protein related to a second protein by descent from a common ancestral protein.

The polypeptides disclosed herein (i.e., SAMD9 polypeptides and M062R polypeptides) may include "variants" of the polypeptides described herein. As used herein, a "variant" refers to a protein having an amino acid sequence that differs from a reference sequence. A variant may have one or more insertions, deletions, or substitutions of an amino acid residue relative to a reference sequence. For example, an SAMD9 polypeptide variant may have one or more insertion(s), deletion(s), or substitution(s) of at least one amino acid residue relative to the reference SAMD9 polypeptide (SEQ ID NO: 1) disclosed herein. In some embodiments, the SAMD9 polypeptide may include a polypeptide having at least 50%, 55%, 60%, 65%, 70%, 75%, 80%, 85%, 86%, 87%, 88%, 89%, 90%, 91%, 92%, 93%, 94%, 95%, 96%, 97%, 98%, 99%, or 100% sequence identity to SEQ ID NO: 1 (human SAMD9 polypeptide sequence).

Regarding the polypeptides disclosed herein, the phrases "% sequence identity," "percent identity," or "% identity" refer to the percentage of residue matches between at least two amino acid sequences aligned using a standardized algorithm. Methods of amino acid sequence alignment are well-known in the art. A suite of commonly used and freely available sequence comparison algorithms is provided by the National Center for Biotechnology Information (NCBI) Basic Local Alignment Search Tool (BLAST), which is available from several sources, including the NCBI, Bethesda, Md., at its website. The BLAST software suite includes various sequence analysis programs including "blastp," that may be used to align a known amino acid sequence with other amino acids sequences from a variety of databases.

Polypeptide sequence identity may be measured over the length of an entire defined polypeptide sequence, for example, as defined by a particular SEQ ID number, or may be measured over a shorter length, for example, over the length of a fragment taken from a larger, defined polypeptide sequence, for instance, a fragment of at least 15, at least 20, at least 30, at least 40, at least 50, at least 70 or at least 150 contiguous residues. Such lengths are exemplary only, and it is understood that any fragment length supported by the sequences shown herein, in the tables, figures or Sequence Listing, may be used to describe a length over which percentage identity may be measured.

A "deletion" in a polypeptide described herein refers to a change in the amino acid sequence resulting in the absence of one or more amino acid residues. A deletion may remove at least 1, 2, 3, 4, 5, 10, 20, 50, 100, 200, or more amino acids residues. A deletion may include an internal deletion and/or a terminal deletion (e.g., an N-terminal truncation, a C-terminal truncation or both of a reference polypeptide).

"Insertions" and "additions" in a polypeptide described herein refers to changes in an amino acid sequence resulting in the addition of one or more amino acid residues. An insertion or addition may refer to 1, 2, 3, 4, 5, 10, 20, 30, 40, 50, 60, 70, 80, 90, 100, 150, 200, or more amino acid residues. A variant or homolog of a polypeptide described herein may have N-terminal insertions, C-terminal insertions, internal insertions, or any combination of N-terminal insertions, C-terminal insertions, and internal insertions.

Suitable "cells" in accordance with the present invention may include eukaryotic cells. Suitable eukaryotic cells include, without limitation, animal cells. In some embodiments, the cell is a mammalian cell such as, without limitation, a mouse cell, a rat cell, a hamster cell, or a human cell. The cell may be a cell line used to produce viral particles or viruses including, without limitation, mammalian cell lines such as A549 cells, THP1 cells, HeLa cells, CHO cells, HEK293 cells, HEK293T cells, COS cells, BK cells, MDCK cells, PER C6 cells, HKB-11 cells, CAP (CEVEC's Amniocyte Production) cells, Huh 7 cells, human diploid cells, HT-1080 cells, and Vero cells.

The eliminated or reduced activity or expression of the SAMD9 polypeptide is relative to a control cell. A "control cell" is a wild-type cell that has not been modified as described herein and may include a wild-type SAMD9 gene encoding a wild-type SAMD9 polypeptide. Exemplary control cells may include wild-type A549 cells, THP1 cells, or HeLa cells. The control cell may be the same type of cell as the cell modified to eliminate or reduce the activity or expression of a SAMD9 polypeptide.

As used herein, the "activity" of a SAMD9 polypeptide refers to any of the biological functions of a SAMD9 polypeptide including, without limitation, inflammatory or anti-viral functions. In some embodiments, the activity of the SAMD9 polypeptide is reduced by at least 30%, 40%, 50%, 55%, 60%, 65%, 70%, 75%, 80%, 85%, 90%, 95%, or 99%, or more as compared to a control cell.

As used herein, the term "expression" may refer either to the levels of an RNA encoding a protein in a cell or the levels of the protein in a cell.

In some embodiments, the expression of the SAMD9 polypeptide is reduced by at least 30%, 40%, 50%, 55%, 60%, 65%, 70%, 75%, 80%, 85%, 90%, 95%, or 99%, or more as compared to a control cell. In a preferred example, the SAMD9 is reduced at least 60% or more, preferably 80% or more.

The cells may be modified to eliminate or reduce as compared to a control cell the activity or expression of a SAMD9 polypeptide described herein. As used herein, the terms "modified" or "modifying" refer to using any laboratory methods available to those of skill in the art including, without limitation, genetic engineering techniques (i.e. CRISPR/Cas techniques or gene silencing technologies) or forward genetic techniques to affect the activity or expression of a SAMD9 polypeptide. It will be readily apparent to one of ordinary skill in the art that there are multiple potential ways to eliminate or reduce the activity or expression of a SAMD9 polypeptide in a cell by modifying the gene encoding the SAMD9 polypeptide by, for example, introducing targeted mutations, by modifying a mRNA (or levels thereof) encoding the SAMD9 polypeptide, for example, by using gene silencing techniques, or by inhibiting the SAMD9 polypeptide at the protein level.

In some embodiments, the cell may include a nucleic acid agent capable of downregulating an RNA transcript encoding the SAMD9 polypeptide. Suitable nucleic acid agents may include, without limitation, a short hairpin RNA (shRNA), microRNA, siRNA, or antisense RNA.

As exemplarily, nucleic acid agents capable of downregulating an RNA transcript encoding the SAMD9 polypeptide, in the Examples, the inventors use a short hairpin RNA (shRNA) targeting SAMD9 mRNAs in THP1 cells.

The cell may also be modified to introduce a hypomorphic mutation or a null mutation in a polynucleotide (i.e., gene) encoding the SAMD9 polypeptide. A "null mutation" is an alteration in a gene that results in a gene that completely lacks its normal function. The complete lack of function may be the result of the complete absence of a gene product (i.e., protein or RNA) being produced in a cell or may result from the expression of a non-functional polypeptide. Similarly, a "hypomorphic mutation" is an alteration in a gene that results in a gene that has reduced activity. The reduced activity may be from a reduced level of expression of gene products (i.e., protein or RNA) from the gene or may result from the expression of a gene product (i.e. protein or RNA) that has reduced functional activity. For example, the gene product (i.e., protein or RNA) may result in a truncated form of the SAMD9 protein that has reduced or eliminated all functionality within a cell, as demonstrated in the examples.

It will be readily apparent to those of skill in the art that a variety of null or hypomorphic mutations may be introduced (using, for example, CRISPR/Cas or other genetic engineering techniques) into a polynucleotide encoding the SAMD9 polypeptides described herein to arrive at embodiments of the present invention. For example, early stop codons may be introduced into the open reading frame of the gene encoding the SAMD9 polypeptide, which would result in the expression of a shorter protein sequence completely lacking or having reduced activity. Alternatively or additionally, a person of ordinary skill may introduce alterations (i.e., substitutions or deletions) into the promoter of a gene encoding the SAMD9 polypeptide described herein that result in little or no expression of the SAMD9 polypeptide.

Figure 1:
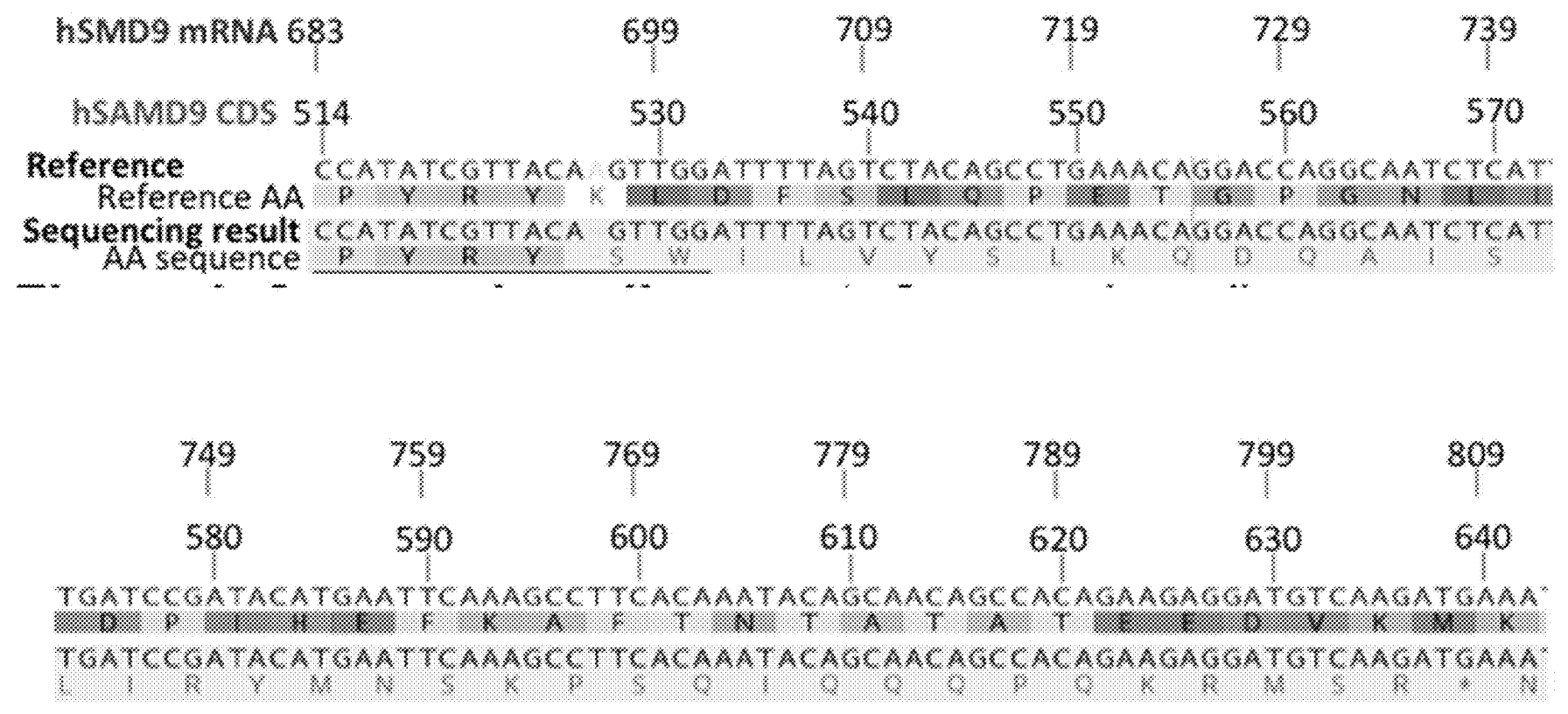
Figure 7:
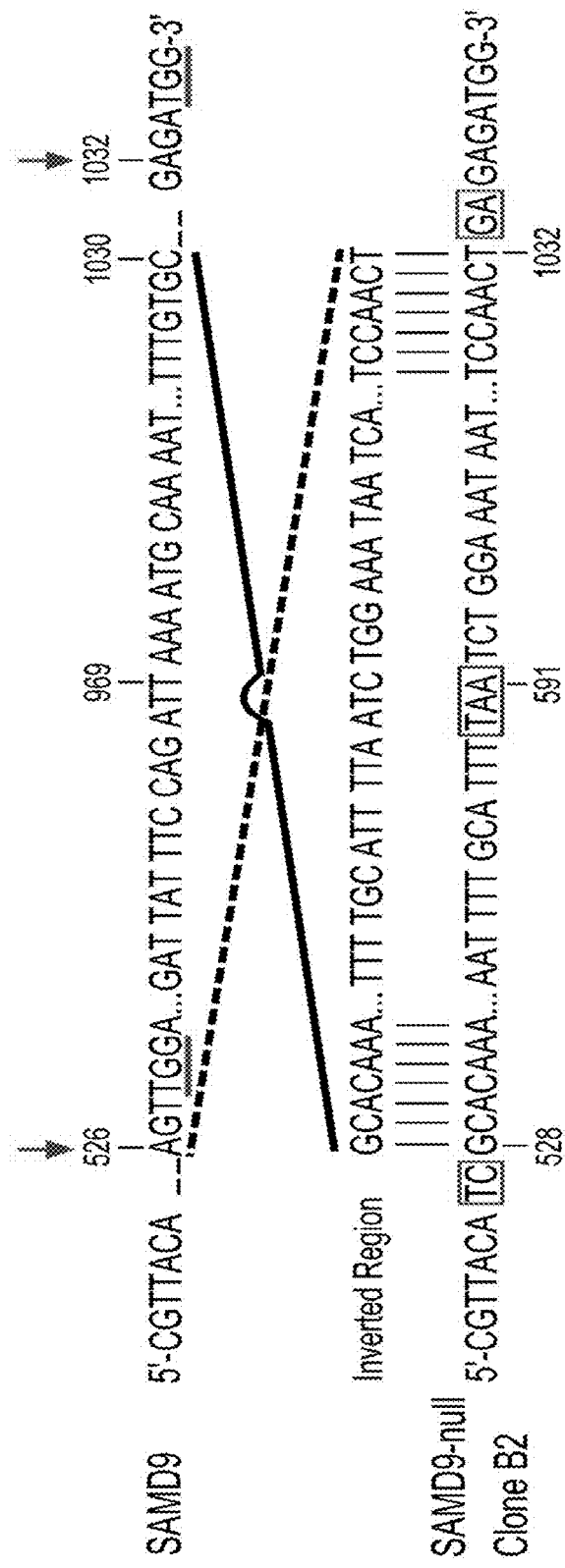
FIG. 7 CRISPR-Cas9 knockout of SAMD9 with 2 different guide RNAs (gRNAs) causing inversion at the targeted region. SAMD9 sequence is a representation of the human SAMD9 CDS. Cleavage at right after both the nucleotides 526 and 1030 guided by gRNAs (arrows) led to addition of nucleotides (squares) during DNA repair and DNA inversion (black solid and dotted lines) in the genome. This reconfiguration of the SAMD9 sequence generated a stop codon (square) at the current location of 591 nucleotides, which caused SAMD9 expression knockout. The resulting truncated and mutant SAMD9 was not detectable using the SAMD9 antibody (SigmaAldrich Catalog #HPA021319) that recognizes the N-terminal of the protein (1-82 amino acids or aa). Underline labeled nucleotides are the PAM sequence. To illustrate the inversion, SAMD9 reverse complementary sequence between the gRNA targets was shown in comparison to SAMD9-null (B2 clone). Squares specify inserted nucleotides with codon frameshift. The square indicates stop codon at nucleotide position 591.

As exemplarily null or hypomorphic mutations that may be introduced into a gene encoding a SAMD9 polypeptide described herein, in the Examples, the inventors use CRISPR/Cas9 molecular tools to introduce a premature stop codon into the SAMD9 gene, which led to the production of a truncated protein (see, e.g., FIG. 1 wherein the introduction of a single nucleotide caused a frame shift and premature stop codon). CRISPR/Cas9 molecular tools was also used to knockout of SAMD9 with 2 different guide RNAs (gRNAs) causing inversion at the targeted region as demonstrated in the Examples and FIG. 7. Thus, suitable cells may produce a truncated form of the SAMD9 protein that has reduced or eliminated its activity.

Still further modifications contemplated herein include mutations that impact one or more of the activities of the SAMD9 polypeptide. The SAMD9 polypeptide has inflammatory and anti-viral functional activities. It will be understood by those of skill in the art that alterations (i.e., mutations and/or deletions) could be made to the SAMD9 polypeptide that would be expected to eliminate or reduce an activity of the SAMD9 polypeptide.

Methods

In another aspect, the present invention relates to methods of producing a virus. The methods may include introducing the virus into any of the cells described herein.

The virus may be "introduced" into the cell by, for example, contacting the cell with viral particles or introducing a polynucleotide including a viral polynucleotide into the cell (i.e., DNA plasmid). Methods of introducing polynucleotides into a cell are known in the art and may include, without limitation, microinjection, transformation, and transfection methods. Transformation or transfection may occur under natural or artificial conditions according to various methods well known in the art, and may rely on any known method for the insertion of foreign nucleic acid sequences into a host cell. The method for transformation or transfection is selected based on the type of host cell being transformed and may include, but is not limited to, bacteriophage or viral infection, electroporation, heat shock, lipofection, and particle bombardment. Microinjection of polynucleotides may also be used to introduce polynucleotides into cells.

In the nonlimiting Examples, the present inventors introduce viruses (i.e., myxoma and herpes simplex viruses) into the cells described herein by incubating cells with viruses on ice, at room temperature, or at 37° C. in regular medium for an hour followed by removing inoculum and replishing with standard growth medium for infection development. For myxoma and herpes simplex viruses, the present inventors used natural infections in conventional cell culture.

The cells described herein, e.g., cells with a modified SAMD9 (e.g., SAM9D null cells or truncated non-active or reduced SAMD9 activity), are shown to produce an increase in virus infectivity and thus the ability to increase the production of the amount of virus made in vitro for laboratory and clinical purposes.

Optionally, the methods may also further include purifying the virus from the cell. The term "purifying" is used to refer to the process of ensuring that the virus or viral particles are substantially or essentially free from cellular components and/or other impurities. Purification of viruses or viral particles is typically performed using molecular biology and analytical chemistry techniques such as, without limitation, ultracentrifugation, density gradient (i.e., sucrose gradient), chromatography, precipitation and/or filtration. Methods of purifying viruses or viral particles are well known to those skilled in the art. A "purified" virus or viral particles means that the virus or viral particles is at least 85% pure, more preferably at least 95% pure, and most preferably at least 99% pure.

As used herein, a "virus" may be any virus having DNA or RNA genomes. Suitable viruses may include, without limitation, myxoma viruses, herpes simplex viruses, rotaviruses, reoviruses, influenza viruses or adenoviruses.

As shown in the examples, the altered SAMD9 cells are able to substantially increase the viral titer production for a number of viruses within the in vitro cultures. The present cells are able to increase the virus titer production by at least 1 log (10 fold), in some examples, at least 2 log (100 fold) as compared to the wildtype cells. For example, for rotaviruses, a greater than a log increase in virus titers (e.g., number of viral genomes produced by the cells) was seen. In some examples, the altered SAMD9 cells were able to produce a greater than 2 log increase in virus production with the altered SAMD9 cells (ΔSAMD9 HeLa cells) (about 100 fold increase) as compare to wildtype cells. In some examples, the virus titer was able to go from an undetectable level within wildtype cells to a detectable level (e.g. 103 genomes) when using the altered SAMD9 cells.

Altering the SAMD9 production in any cell was able to increase the ability of that altered cell to produce viruses. The inventors discovered that the greater the reduction of SAMD9 activity within the cells, the greater an increase in the ability to produce virus (i.e. increase virus production and titer). For example, in one exemplary cell type, a 60% reduction of SAM9 activity within a cell resulted, in some examples, in a log (10 fold) increase in virus titer.

Viral titer, viral particles, or infectious particles in a given volume (e.g., per mL) can be measured by any method known in the art. For example, the number of genomes can be quantitated within the supernatant from the altered cells using methods known in the art. For example, nucleic acid based tests can be used (i.e. RNA copies per mL), which include, but are not limited to, for example, PCR, RT-PCR, viral plaque assay, etc., tittering assay (e.g., serial dilution, etc.), and are well within one skilled in the art to determine.

In some embodiments, the virus may include a mutation affecting the growth of the virus (i.e., replication-incompetent). Exemplary viruses including a mutation affecting the growth of the viruses may include, without limitation, myxoma viruses including a hypomorphic or a null mutation in a M062R polynucleotide encoding a M062R polypeptide. See Liu et al., *J. Virol.* 85(7):3270-3282 (2011) and International Application No. PCT/US19/33973 all of which are incorporated herein by reference in their entirety. Myxoma virus protein M062R is an immunoregulatory protein in myxoma viruses. M062R is a functional homolog of the C7L family of host range genes from orthpoxviruses and is required for MYVX replication in most human cancer cells.

Exemplary viruses including a mutation affecting the growth of the viruses may include, without limitation, mutant viruses that lose an inhibitor of SAMD9 activity.

The present disclosure is not limited to the specific details of construction, arrangement of components, or method steps set forth herein. The compositions and methods disclosed herein are capable of being made, practiced, used, carried out and/or formed in various ways that will be apparent to one of skill in the art in light of the disclosure that follows. The phraseology and terminology used herein is for the purpose of description only and should not be regarded as limiting to the scope of the claims. Ordinal indicators, such as first, second, and third, as used in the description and the claims to refer to various structures or method steps, are not meant to be construed to indicate any specific structures or steps, or any particular order or configuration to such structures or steps. All methods described herein can be performed in any suitable order unless otherwise indicated herein or otherwise clearly contradicted by context. The use of any and all examples, or exemplary language (e.g., "such as") provided herein, is intended merely to facilitate the disclosure and does not imply any limitation on the scope of the disclosure unless otherwise claimed. No language in the specification, and no structures shown in the drawings, should be construed as indicating that any non-claimed element is essential to the practice of the disclosed subject matter. The use herein of the terms "including," "comprising," or "having," and variations thereof, is meant to encompass the elements listed thereafter and equivalents thereof, as well as additional elements. Embodiments recited as "including," "comprising," or "having" certain elements are also contemplated as "consisting essentially of" and "consisting of" those certain elements.

Recitation of ranges of values herein are merely intended to serve as a shorthand method of referring individually to each separate value falling within the range, unless otherwise indicated herein, and each separate value is incorporated into the specification as if it were individually recited herein. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this disclosure. Use of the word "about" to describe a particular recited amount or range of amounts is meant to indicate that values very near to the recited amount are included in that amount, such as values that could or naturally would be accounted for due to manufacturing tolerances, instrument and human error in forming measurements, and the like. All percentages referring to amounts are by weight unless indicated otherwise.

No admission is made that any reference, including any non-patent or patent document cited in this specification, constitutes prior art. In particular, it will be understood that, unless otherwise stated, reference to any document herein does not constitute an admission that any of these documents forms part of the common general knowledge in the art in the United States or in any other country. Any discussion of the references states what their authors assert, and the applicant reserves the right to challenge the accuracy and pertinence of any of the documents cited herein. All references cited herein are fully incorporated by reference in their entirety, unless explicitly indicated otherwise. The present disclosure shall control in the event there are any disparities between any definitions and/or description found in the cited references.

Unless otherwise specified or indicated by context, the terms "a", "an", and "the" mean "one or more." For example, "a protein" or "an RNA" should be interpreted to mean "one or more proteins" or "one or more RNAs," respectively.

The following examples are meant only to be illustrative and are not meant as limitations on the scope of the invention or of the appended claims.

EXAMPLES

Example 1

Sterile α motif-domain containing protein 9 (SAMD9) is an important protein that plays critical roles in human health. We previously found that SAMD9 has antiviral function against poxviruses and poxviruses have evolved many viral proteins to inhibit SAMD9 function.[1, 2] During infection by myxoma virus (MYXV) one viral protein M062 takes the role to neutralize SAMD9. Without M062, MYXV infection cannot proceed resulting in an abortive infection. This is a form of infection in which viral genome replication is not complete and expression of many viral genes cannot be accomplished. However, by knocking down the mRNA level of SAMD9, we can restore partially the infection by a M062R-null MYXV.[1] Interestingly, we found that in human A549 cells by deleting SAMD9 expression, we not only can restore M062R-null MYXV infection to the same levels as the replicating MYXV but also can drastically improve the viral yield of replicating MYXV (e.g., WT virus). We also found that knocking down SAMD9 mRNA level led to improved viral yield by herpes simplex virus type 1 (HSV-1). Thus cells without SAMD9 expression can be very useful for the production of viruses (e.g., MYXV and HSV-1) for clinical applications.

We engineered SAMD9-null cells with CRISPR/CAS9 technology and one example on how to engineer the cell line is described below. We first designed the guide RNAs (gRNAs) and chose two options as following: gRNA1-Forward: 5'-CACCGtaatccatatcgttacaagt-3' (SEQ ID NO: 2); gRNA1-Reverse: 5'-AAACacttgtaacgatatggattaC-3' (SEQ ID NO: 3); gRNA2-Forward: 5'-CACCGtctcactat-ttgtgcgagat-3' (SEQ ID NO: 4); gRNA2-Reverse: 5'-AAA-CatctcgcacaaatagtgagaC-3' (SEQ ID NO: 5). We cloned gRNA1 and 2 into vector pX330-U6-Chimeric_BB-CBh-hSpCas9 (Addgene plasmid #42230)[3] and pSpCas9 (BB)-2A-GFP (PX458) (Addgene plasmid #48138)[4], respectively. After cotransfection of both constructs, single cells that turned green were individually collected via cell sorting and cultured to expand. Western blot was conducted to confirm the absence of SAMD9 protein as previously described.[5] Briefly, both plasmids expressing gRNA1 and 2 are transfected into cells and followed by cell sorting of GFP positive cells at 24 h post-transfection. GFP expression indicated that transfected cells expressed at least Cas9-GFP and gRNA 2. It is most likely that transfected cells received both sets of Cas9 and gRNA. Single clones are obtained in 96-well-plates for amplification and a pooled cell population was also obtained and frozen as previously described.[6] The GFP expression was only transient and the plasmids expressing Cas9-gRNA were lost in the cells while cells continued to divide. Once the single cell clone is confirmed to no longer express SAMD9 protein, we sequenced the genomic DNA of SAMI) 9 to confirm the genetic manipulation was successful. We found that the most frequent cause of SAMD9 deletion was caused by cleavage guided by gRNA1 and the example is shown in FIG. 1, which is from a single cell clone of A549 SAMD9-null cells. The Western blot result is shown in FIG. 2.

We next tested M062R-null cell infection in these cells and found that viral replication was completely restored to comparable levels of WT MYXV infection (FIG. 3).

We also found that once SAMD9 is deleted from human cells, WT myxoma virus (MYXV) infection is also significantly improved. See, e.g., FIG. 4 and FIGS. 5A-5D. For example in SAMD9-null cells of HeLa and A549 cells, WT MYXV replication increased ranging from 5 fold to up to a log (FIG. 4 and FIG. 5D).

We also tested whether knocking-down SAMD9 expression in another human cell line, THP1, could increase HSV-1 infection. HSV-1 infection was conducted in PMA-differentiated THP1 cells (ATCCC TIB-202™) and at given time points cell lysates were collected for titration on RS cells as previously described.[8] SAMD9 knockdown cells were engineered using lentivirus expressing shRNAs targeting SAMD9 mRNA and the control cells were engineered using lentivirus expressing control shRNAs; to engineer these cell lines we utilized a method similar to what has been reported.[2] Reduced SAMD9 protein levels were observed in cells stably expressing SAMD9 targeting shRNAs, while introduction of non-targeting shRNAs (control) did not affect SAMD9 expression. See FIG. 6B. We found that knocking-down SAMD9 improved HSV-1 infection. See FIG. 6A.

FIG. 7 describes a second method of knocking down using CRISPR-Cas9 knockout of SAMD9 with 2 different guide RNAs (gRNAs) causing inversion at the targeted region. SAMI) 9 sequence is a representation of the human SAMD9 CDS. Cleavage at right after both the nucleotides 526 and 1030 guided by gRNAs (arrows) led to addition of nucleotides (squares) during DNA repair and DNA inversion (black solid and dotted lines) in the genome. This reconfiguration of the SAMI) 9 sequence generated a stop codon (square) at the current location of 591 nucleotides, which caused SAMD9 expression knockout. The resulting truncated and mutant SAMD9 was not detectable using the SAMD9 antibody (SigmaAldrich Catalog #HPA021319) that recognizes the N-terminal of the protein (1-82 amino acids or aa). Underline labeled nucleotides are the PAM sequence. To illustrate the inversion, SAMD9 reverse complementary sequence between the gRNA targets was shown in comparison to SAMD9-null (B2 clone). Squares specify inserted nucleotides with codon frameshift. The square indicate stop codon at nucleotide position 591.

Materials and Methods

Cell Lines and Viruses

A549 (ATCC® CCL-185™), THP1 (ATCCC) TIB-202™), BSC40 (ATCC® CRL-2761) and HeLa (ATCC® CCL-2") were obtained from ATCC. While THP1 cells have been cultured in RMPI1640 (Lonza, BioWhittaker) supplemented with 10% fetal bovine serum (FBS; Atlantic Biological) and 100 μg of penicillin-streptomycin (pen/strep; Invitrogen)/ml, A549, BSC-40 and HeLa are cultured in Dulbecco minimum essential medium (DMEM; Invitrogen) supplemented with 10% FBS, 2 mM glutamine (Invitrogen) and 100 μg of pen/Sterp per ml. RS cells and HSV-1 ($17syn^+$) were kindly provided by Dr. David Bloom (University of Florida). HSV-1 was amplified in RS cells and the titer is determined on RS cells using plaque assay as previously described (Liu et al., 2008). Wildtype MYXV and M062R-null MYXV have been reported previously (Liu et al., 2011). These MYXVs were amplified on BSC-40 and titers were determined on BSC-40 cells as previous described (Liu et al., 2011).

Antibodies and Reagents

Antibodies for SAMD9 (SigmaAldrich), SAMD9L (SigmaAldrich), β-actin (SigmaAldrich), goat anti-rabbit IgG-HRP, and goat anti-mouse IgG-HRP were used for the Western Bloting. Actinomycin D, cytosine beta-D-arabinofuranoside, MG132 (Z-Leu-Leu-Leu-al) were purchased from SigmaAldrich and resuspended for storage according to Cold Spring Harbor Protocols. Luciferase activity was detected using Luciferase Assay System (Promega).

Sequencing to Confirm SAMD9 Deletion

Cell genomic DNA was extracted using PureLink Genomic DNA Mini Kit (Invitrogen). PCR amplification of SAMD9 intron free region using Phusion High-Fidelity DNA polymerase (New England Biolabs) and the primer set of (5'-SAMD9F78 AGTCggtaccGCCATTGAAGATTC-GATT-3') (SEQ ID NO: 10) and SAMD9R724 (5'-GACTctcgagttaAGAATCTGCACAGTTTTGAA-3') (SEQ ID NO: 11) to generate a fragment of approximately 1938 nt. This DNA fragment was then cloned into a plasmid using Zero Blunt TOPO cloning kit (ThermoFisher Scientific). Sequencing was conducted using M13 forward and reverse primers.

REFERENCES

1. Liu J, Wennier S, Zhang L, McFadden G. M062 is a host range factor essential for myxoma virus pathogenesis and functions as an antagonist of host SAMD9 in human cells. *Journal of virology* 2011, 85 (7): 3270-3282.
2. Liu J, McFadden G. SAMD9 is an innate antiviral host factor with stress response properties that can be antagonized by poxviruses. *Journal of virology* 2015, 89 (3): 1925-1931.
3. Cong L, Ran F A, Cox D, Lin S, Barretto R, Habib N, et al. Multiplex genome engineering using CRISPR/Cas systems. *Science* (*New York, NY*) 2013, 339 (6121): 819-823.
4. Ran F A, Hsu P D, Wright J, Agarwala V, Scott D A, Zhang F. Genome engineering using the CRISPR-Cas9 system. *Nature protocols* 2013, 8 (11): 2281-2308.
5. Nounamo B, Li Y, O'Byrne P, Kearney A M, Khan A, Liu J. An interaction domain in human SAMD9 is essential for myxoma virus host-range determinant M062 antagonism of host anti-viral function. *Virology* 2017, 503:94-102.
6. Bauer D E, Canver M C, Orkin S H. Generation of genomic deletions in mammalian cell lines via CRISPR/Cas9. *Journal of visualized experiments: JoVE* 2015(95): e52118.
7. Villa N Y, Bartee E, Mohamed M R, Rahman M M, Barrett J W, McFadden G. Myxoma and vaccinia viruses exploit different mechanisms to enter and infect human cancer cells. *Virology* 2010, 401(2): 266-279.
8. Liu J, Lewin A S, Tuli S S, Ghivizzani S C, Schultz G S, Bloom D C. Reduction in severity of a herpes simplex virus type 1 murine infection by treatment with a ribozyme targeting the UL20 gene RNA. *Journal of virology* 2008, 82 (15): 7467-7474.

I claim:

1. A method of producing a virus comprising introducing a virus into a modified cell, wherein the cell is modified to eliminate or reduce the activity or expression of a Sterile α motif-domain containing protein 9 (SAMD9) polypeptide as compared to a control cell, and wherein the virus is selected from the group consisting of a herpes simplex virus, a rotavirus, a reovirus, an influenza virus, and an adenovirus and wherein the modified cell produces at least a $\log_{10}$ increase in virus titer as compared with a control cell.

2. The method of claim 1, further comprising purifying the virus from the cell.

3. The method of claim 1, wherein the virus comprises a mutation affecting the growth of the virus.

4. The method of claim 1, wherein the cell is an A549.

5. The method of claim 1, wherein the cell is a THP1 cell.

* * * * *

SEQUENCE LISTING

<160> NUMBER OF SEQ ID NOS: 14

<210> SEQ ID NO 1
<211> LENGTH: 1589
<212> TYPE: PRT
<213> ORGANISM: Homo sapiens
<220> FEATURE:
<221> NAME/KEY: MISC_FEATURE
<222> LOCATION: (1)..(1589)
<223> OTHER INFORMATION: Human SAMD9 polypeptide

<400> SEQUENCE: 1

Met Ala Lys Gln Leu Asn Leu Pro Glu Asn Thr Asp Asp Trp Thr Lys
1               5                   10                  15

Glu Asp Val Asn Gln Trp Leu Glu Ser His Lys Ile Asp Gln Lys His
            20                  25                  30

Arg Glu Ile Leu Thr Glu Gln Asp Val Asn Gly Ala Val Leu Lys Trp
        35                  40                  45

Leu Lys Lys Glu His Leu Val Asp Met Gly Ile Thr His Gly Pro Ala
    50                  55                  60

Ile Gln Ile Glu Glu Leu Phe Lys Glu Leu Arg Lys Thr Ala Ile Glu
65                  70                  75                  80

Asp Ser Ile Gln Thr Ser Lys Met Gly Lys Pro Ser Lys Asn Ala Pro
                85                  90                  95

Lys Asp Gln Thr Val Ser Gln Lys Glu Arg Arg Glu Thr Ser Lys Gln
            100                 105                 110

Lys Gln Lys Gly Lys Glu Asn Pro Asp Met Ala Asn Pro Ser Ala Met
        115                 120                 125

Ser Thr Thr Ala Lys Gly Ser Lys Ser Leu Lys Val Glu Leu Ile Glu
    130                 135                 140

Asp Lys Ile Asp Tyr Thr Lys Glu Arg Gln Pro Ser Ile Asp Leu Thr
145                 150                 155                 160

Cys Val Ser Tyr Pro Phe Asp Glu Phe Ser Asn Pro Tyr Arg Tyr Lys
                165                 170                 175

Leu Asp Phe Ser Leu Gln Pro Glu Thr Gly Pro Gly Asn Leu Ile Asp
            180                 185                 190

Pro Ile His Glu Phe Lys Ala Phe Thr Asn Thr Ala Thr Ala Thr Glu
        195                 200                 205

Glu Asp Val Lys Met Lys Phe Ser Asn Glu Val Phe Arg Phe Ala Ser
    210                 215                 220

Ala Cys Met Asn Ser Arg Thr Asn Gly Thr Ile His Phe Gly Val Lys
225                 230                 235                 240

Asp Lys Pro His Gly Lys Ile Val Gly Ile Lys Val Thr Asn Asp Thr
                245                 250                 255

Lys Glu Ala Leu Ile Asn His Phe Asn Leu Met Ile Asn Lys Tyr Phe
            260                 265                 270

Glu Asp His Gln Val Gln Ala Lys Lys Cys Ile Arg Glu Pro Arg
        275                 280                 285

Phe Val Glu Val Leu Leu Pro Asn Ser Thr Leu Ser Asp Arg Phe Val
    290                 295                 300

Ile Glu Val Asp Ile Ile Pro Gln Phe Ser Glu Cys Gln Tyr Asp Tyr
305                 310                 315                 320

Phe Gln Ile Lys Met Gln Asn Tyr Asn Asn Lys Ile Trp Glu Gln Ser
                325                 330                 335

Lys Lys Phe Ser Leu Phe Val Arg Asp Gly Thr Ser Ser Lys Asp Ile
            340                 345                 350

-continued

```
Thr Lys Asn Lys Val Asp Phe Arg Ala Phe Lys Ala Asp Phe Lys Thr
            355                 360                 365
Leu Ala Glu Ser Arg Lys Ala Glu Glu Lys Phe Arg Ala Lys Thr
370                 375                 380
Asn Lys Lys Glu Arg Glu Gly Pro Lys Leu Val Lys Leu Leu Thr Gly
385                 390                 395                 400
Asn Gln Asp Leu Leu Asp Asn Ser Tyr Tyr Glu Gln Tyr Ile Leu Val
                405                 410                 415
Thr Asn Lys Cys His Pro Asp Gln Thr Lys His Leu Asp Phe Leu Lys
                420                 425                 430
Glu Ile Lys Trp Phe Ala Val Leu Glu Phe Asp Pro Gly Ser Asn Ile
            435                 440                 445
Asn Gly Val Val Lys Ala Tyr Lys Glu Ser Arg Val Ala Asn Leu His
        450                 455                 460
Phe Pro Ser Val Tyr Val Glu Gln Lys Thr Thr Pro Asn Glu Thr Ile
465                 470                 475                 480
Ser Thr Leu Asn Leu Tyr His Gln Pro Ser Trp Ile Phe Cys Asn Gly
                485                 490                 495
Arg Leu Asp Leu Asp Ser Glu Lys Tyr Lys Pro Phe Asp Pro Ser Ser
                500                 505                 510
Trp Gln Arg Glu Arg Ala Ser Asp Val Arg Lys Leu Ile Ser Phe Leu
            515                 520                 525
Thr His Glu Asp Ile Met Pro Arg Gly Lys Phe Leu Val Val Phe Leu
        530                 535                 540
Leu Leu Ser Ser Val Asp Asp Pro Arg Asp Pro Leu Ile Glu Thr Phe
545                 550                 555                 560
Cys Ala Phe Tyr Gln Asp Leu Lys Gly Met Glu Asn Ile Leu Cys Ile
                565                 570                 575
Cys Val His Pro His Ile Phe Gln Gly Trp Lys Asp Leu Leu Glu Ala
                580                 585                 590
Arg Leu Ile Lys His Gln Asp Glu Ile Ser Ser Gln Cys Ile Ser Ala
            595                 600                 605
Leu Ser Leu Glu Glu Ile Asn Gly Thr Ile Leu Lys Leu Lys Ser Val
        610                 615                 620
Thr Gln Ser Ser Lys Arg Leu Leu Pro Ser Ile Gly Leu Ser Thr Val
625                 630                 635                 640
Leu Leu Lys Lys Glu Glu Asp Ile Met Thr Ala Leu Glu Ile Ile Cys
                645                 650                 655
Glu Asn Glu Cys Glu Gly Thr Leu Leu Glu Lys Asp Lys Asn Lys Phe
                660                 665                 670
Leu Glu Phe Lys Ala Ser Lys Glu Glu Asp Phe Tyr Arg Gly Gly Lys
            675                 680                 685
Val Ser Trp Trp Asn Phe Tyr Phe Ser Ser Glu Ser Tyr Ser Ser Pro
        690                 695                 700
Phe Val Lys Arg Asp Lys Tyr Glu Arg Leu Glu Ala Met Ile Gln Asn
705                 710                 715                 720
Cys Ala Asp Ser Ser Lys Pro Thr Ser Thr Lys Ile Ile His Leu Tyr
                725                 730                 735
His His Pro Gly Cys Gly Gly Thr Thr Leu Ala Met His Ile Leu Trp
                740                 745                 750
Glu Leu Arg Lys Lys Phe Arg Cys Ala Val Leu Lys Asn Lys Thr Val
            755                 760                 765
```

-continued

```
Asp Phe Ser Glu Ile Gly Glu Gln Val Thr Ser Leu Ile Thr Tyr Gly
770                 775                 780

Ala Met Asn Arg Gln Glu Tyr Val Pro Val Leu Leu Val Asp Asp
785                 790                 795                 800

Phe Glu Glu Gln Asp Asn Val Tyr Leu Leu Gln Tyr Ser Ile Gln Thr
                    805                 810                 815

Ala Ile Ala Lys Lys Tyr Ile Arg Tyr Glu Lys Pro Leu Val Ile Ile
                    820                 825                 830

Leu Asn Cys Met Arg Ser Gln Asn Pro Glu Lys Ser Ala Arg Ile Pro
                    835                 840                 845

Asp Ser Ile Ala Val Ile Gln Gln Leu Ser Pro Lys Glu Gln Arg Ala
850                 855                 860

Phe Glu Leu Lys Leu Lys Glu Ile Lys Glu Gln His Lys Asn Phe Glu
865                 870                 875                 880

Asp Phe Tyr Ser Phe Met Ile Met Lys Thr Asn Phe Asn Lys Glu Tyr
                    885                 890                 895

Ile Glu Asn Val Val Arg Asn Ile Leu Lys Gly Gln Asn Ile Phe Thr
                    900                 905                 910

Lys Glu Ala Lys Leu Phe Ser Phe Leu Ala Leu Leu Asn Ser Tyr Val
                    915                 920                 925

Pro Asp Thr Thr Ile Ser Leu Ser Gln Cys Glu Lys Phe Leu Gly Ile
930                 935                 940

Gly Asn Lys Lys Ala Phe Trp Gly Thr Glu Lys Phe Glu Asp Lys Met
945                 950                 955                 960

Gly Thr Tyr Ser Thr Ile Leu Ile Lys Thr Glu Val Ile Glu Cys Gly
                    965                 970                 975

Asn Tyr Cys Gly Val Arg Ile Ile His Ser Leu Ile Ala Glu Phe Ser
                    980                 985                 990

Leu Glu Glu Leu Lys Lys Ser Tyr  His Leu Asn Lys Ser  Gln Ile Met
                    995                 1000                1005

Leu Asp  Met Leu Thr Glu Asn  Leu Phe Phe Asp Thr  Gly Met Gly
        1010                1015                1020

Lys Ser  Lys Phe Leu Gln Asp  Met His Thr Leu Leu  Leu Thr Arg
        1025                1030                1035

His Arg  Asp Glu His Glu Gly  Glu Thr Gly Asn Trp  Phe Ser Pro
        1040                1045                1050

Phe Ile  Glu Ala Leu His Lys  Asp Glu Gly Asn Glu  Ala Val Glu
        1055                1060                1065

Ala Val  Leu Leu Glu Ser Ile  His Arg Phe Asn Pro  Asn Ala Phe
        1070                1075                1080

Ile Cys  Gln Ala Leu Ala Arg  His Phe Tyr Ile Lys  Lys Lys Asp
        1085                1090                1095

Phe Gly  Asn Ala Leu Asn Trp  Ala Lys Gln Ala Lys  Ile Ile Glu
        1100                1105                1110

Pro Asp  Asn Ser Tyr Ile Ser  Asp Thr Leu Gly Gln  Val Tyr Lys
        1115                1120                1125

Ser Lys  Ile Arg Trp Trp Ile  Glu Glu Asn Gly Gly  Asn Gly Asn
        1130                1135                1140

Ile Ser  Val Asp Asp Leu Ile  Ala Leu Leu Asp Leu  Ala Glu His
        1145                1150                1155

Ala Ser  Ser Ala Phe Lys Glu  Ser Gln Gln Gln Ser  Glu Asp Arg
        1160                1165                1170

Glu Tyr  Glu Val Lys Glu Arg  Leu Tyr Pro Lys Ser  Lys Arg Arg
```

```
            1175                 1180                 1185
Tyr Asp Thr Tyr Asn Ile Ala Gly Tyr Gln Gly Glu Ile Glu Val
    1190                 1195                 1200
Gly Leu Tyr Thr Ile Gln Ile Leu Gln Leu Ile Pro Phe Phe Asp
    1205                 1210                 1215
Asn Lys Asn Glu Leu Ser Lys Arg Tyr Met Val Asn Phe Val Ser
    1220                 1225                 1230
Gly Ser Ser Asp Ile Pro Gly Asp Pro Asn Asn Glu Tyr Lys Leu
    1235                 1240                 1245
Ala Leu Lys Asn Tyr Ile Pro Tyr Leu Thr Lys Leu Lys Phe Ser
    1250                 1255                 1260
Leu Lys Lys Ser Phe Asp Phe Asp Glu Tyr Phe Val Leu Leu
    1265                 1270                 1275
Lys Pro Arg Asn Asn Ile Lys Gln Asn Glu Glu Ala Lys Thr Arg
    1280                 1285                 1290
Arg Lys Val Ala Gly Tyr Phe Lys Lys Tyr Val Asp Ile Phe Cys
    1295                 1300                 1305
Leu Leu Glu Glu Ser Gln Asn Asn Thr Gly Leu Gly Ser Lys Phe
    1310                 1315                 1320
Ser Glu Pro Leu Gln Val Glu Arg Cys Arg Arg Asn Leu Val Ala
    1325                 1330                 1335
Leu Lys Ala Asp Lys Phe Ser Gly Leu Leu Glu Tyr Leu Ile Lys
    1340                 1345                 1350
Ser Gln Glu Asp Ala Ile Ser Thr Met Lys Cys Ile Val Asn Glu
    1355                 1360                 1365
Tyr Thr Phe Leu Leu Glu Gln Cys Thr Val Lys Ile Gln Ser Lys
    1370                 1375                 1380
Glu Lys Leu Asn Phe Ile Leu Ala Asn Ile Ile Leu Ser Cys Ile
    1385                 1390                 1395
Gln Pro Thr Ser Arg Leu Val Lys Pro Val Glu Lys Leu Lys Asp
    1400                 1405                 1410
Gln Leu Arg Glu Val Leu Gln Pro Ile Gly Leu Thr Tyr Gln Phe
    1415                 1420                 1425
Ser Glu Pro Tyr Phe Leu Ala Ser Leu Leu Phe Trp Pro Glu Asn
    1430                 1435                 1440
Gln Gln Leu Asp Gln His Ser Glu Gln Met Lys Glu Tyr Ala Gln
    1445                 1450                 1455
Ala Leu Lys Asn Ser Phe Lys Gly Gln Tyr Lys His Met His Arg
    1460                 1465                 1470
Thr Lys Gln Pro Ile Ala Tyr Phe Phe Leu Gly Lys Gly Lys Arg
    1475                 1480                 1485
Leu Glu Arg Leu Val His Lys Gly Lys Ile Asp Gln Cys Phe Lys
    1490                 1495                 1500
Lys Thr Pro Asp Ile Asn Ser Leu Trp Gln Ser Gly Asp Val Trp
    1505                 1510                 1515
Lys Glu Glu Lys Val Gln Glu Leu Leu Leu Arg Leu Gln Gly Arg
    1520                 1525                 1530
Ala Glu Asn Asn Cys Leu Tyr Ile Glu Tyr Gly Ile Asn Glu Lys
    1535                 1540                 1545
Ile Thr Ile Pro Ile Thr Pro Ala Phe Leu Gly Gln Leu Arg Ser
    1550                 1555                 1560
Gly Arg Ser Ile Glu Lys Val Ser Phe Tyr Leu Gly Phe Ser Ile
    1565                 1570                 1575
```

```
Gly Gly  Pro Leu Ala Tyr Asp  Ile Glu Ile Val
    1580                1585

<210> SEQ ID NO 2
<211> LENGTH: 25
<212> TYPE: DNA
<213> ORGANISM: Artificial Sequence
<220> FEATURE:
<223> OTHER INFORMATION: Synthetic- gRNA1 Forward

<400> SEQUENCE: 2
caccgtaatc catatcgtta caagt                                          25

<210> SEQ ID NO 3
<211> LENGTH: 25
<212> TYPE: DNA
<213> ORGANISM: Artificial Sequence
<220> FEATURE:
<223> OTHER INFORMATION: Synthetic- gRNA1 Reverse

<400> SEQUENCE: 3
aaacacttgt aacgatatgg attac                                          25

<210> SEQ ID NO 4
<211> LENGTH: 25
<212> TYPE: DNA
<213> ORGANISM: Artificial Sequence
<220> FEATURE:
<223> OTHER INFORMATION: Synthetic- gRNA2 Forward

<400> SEQUENCE: 4
caccgtctca ctatttgtgc gagat                                          25

<210> SEQ ID NO 5
<211> LENGTH: 25
<212> TYPE: DNA
<213> ORGANISM: Artificial Sequence
<220> FEATURE:
<223> OTHER INFORMATION: Synthetic- gRNA2 Reverse

<400> SEQUENCE: 5
aaacatctcg cacaaatagt gagac                                          25

<210> SEQ ID NO 6
<211> LENGTH: 129
<212> TYPE: DNA
<213> ORGANISM: Homo sapiens
<220> FEATURE:
<221> NAME/KEY: misc_feature
<222> LOCATION: (1)..(129)
<223> OTHER INFORMATION: SAMD9 polynucleotide reference sequence

<400> SEQUENCE: 6
ccatatcgtt acaagttgga ttttagtcta cagcctgaaa caggaccagg caatctcatt    60
gatccgatac atgaattcaa agccttcaca aatacagcaa cagccacaga agaggatgtc   120
aagatgaaa                                                          129

<210> SEQ ID NO 7
<211> LENGTH: 43
<212> TYPE: PRT
<213> ORGANISM: Homo sapiens
<220> FEATURE:
<221> NAME/KEY: MISC_FEATURE
<222> LOCATION: (1)..(43)
<223> OTHER INFORMATION: SAMD9 amino acid reference sequence
```

<400> SEQUENCE: 7

Pro Tyr Arg Tyr Lys Leu Asp Phe Ser Leu Gln Pro Glu Thr Gly Pro
1               5                   10                  15

Gly Asn Leu Ile Asp Pro Ile His Glu Phe Lys Ala Phe Thr Asn Thr
            20                  25                  30

Ala Thr Ala Thr Glu Glu Asp Val Lys Met Lys
        35                  40

<210> SEQ ID NO 8
<211> LENGTH: 128
<212> TYPE: DNA
<213> ORGANISM: Homo sapiens
<220> FEATURE:
<221> NAME/KEY: misc_feature
<222> LOCATION: (1)..(128)
<223> OTHER INFORMATION: Result of sequencing genomic DNA encoding SAMD9
      from a representative clone (E1) of SAMD9-null cells

<400> SEQUENCE: 8
ccatatcgtt acagttggat tttagtctac agcctgaaac aggaccaggc aatctcattg      60
atccgataca tgaattcaaa gccttcacaa atacagcaac agccacagaa gaggatgtca    120
agatgaaa                                                              128

<210> SEQ ID NO 9
<211> LENGTH: 41
<212> TYPE: PRT
<213> ORGANISM: Homo sapiens
<220> FEATURE:
<221> NAME/KEY: MISC_FEATURE
<222> LOCATION: (1)..(41)
<223> OTHER INFORMATION: Translation of the sequencing result of SEQ ID
      NO: 8

<400> SEQUENCE: 9

Pro Tyr Arg Tyr Ser Trp Ile Leu Val Tyr Ser Leu Lys Gln Asp Gln
1               5                   10                  15

Ala Ile Ser Leu Ile Arg Tyr Met Asn Ser Lys Pro Ser Gln Ile Gln
            20                  25                  30

Gln Gln Pro Gln Lys Arg Met Ser Arg
        35                  40

<210> SEQ ID NO 10
<211> LENGTH: 28
<212> TYPE: DNA
<213> ORGANISM: Artificial Sequence
<220> FEATURE:
<223> OTHER INFORMATION: Synthetic- "SAMD9F78" primer for PCR
      amplification of SAMD9 intron free region

<400> SEQUENCE: 10
agtcggtacc gccattgaag attcgatt                                        28

<210> SEQ ID NO 11
<211> LENGTH: 33
<212> TYPE: DNA
<213> ORGANISM: Artificial Sequence
<220> FEATURE:
<223> OTHER INFORMATION: Synthetic- "SAMD9R724" primer for PCR
      amplification of SAMD9 intron free region

<400> SEQUENCE: 11
gactctcgag ttaagaatct gcacagtttt gaa                                  33

<210> SEQ ID NO 12
<211> LENGTH: 4770
<212> TYPE: DNA
<213> ORGANISM: Homo sapiens
<220> FEATURE:
<221> NAME/KEY: misc_feature
<222> LOCATION: (1)..(4470)
<223> OTHER INFORMATION: Coding sequence (CDS) of SAMD9

<400> SEQUENCE: 12

| | | | | | |
|---|---|---|---|---|---|
| atggcaaagc | aacttaacct | tccagaaaat | acagatgatt | ggacaaaaga | ggatgtaaat | 60 |
| cagtggttag | aaagtcataa | gattgaccaa | aaacacaggg | aaattttgac | tgaacaagac | 120 |
| gtgaatggag | cagtcttgaa | gtggttaaaa | aagaacatc | ttgttgatat | gggcatcaca | 180 |
| catggaccag | ctattcaaat | agaagaacta | ttcaaagaat | tgcggaaaac | agccattgaa | 240 |
| gattcgattc | agacatctaa | gatgggaaag | cccagtaaaa | atgctcctaa | agaccaaact | 300 |
| gtgtctcaaa | aggaacgtag | agaaacttca | aagcaaaaac | aaaagggtaa | agagaaccca | 360 |
| gatatggcta | atccgtctgc | aatgagtaca | actgctaaag | gttctaagtc | actaaaagtt | 420 |
| gagctcatag | aagataaaat | agattataca | aaggaaaggc | aaccatccat | agacctgaca | 480 |
| tgtgtatcat | atccatttga | tgaattcagt | aatccatatc | gttacaagtt | ggattttagt | 540 |
| ctacagcctg | aaacaggacc | aggcaatctc | attgatccga | tacatgaatt | caaagccttc | 600 |
| acaaatacag | caacagccac | agaagaggat | gtcaagatga | aatttagcaa | tgaggttttc | 660 |
| cgatttgctt | cagcttgtat | gaattcacgt | accaatggca | ctattcattt | tggagtcaaa | 720 |
| gacaaacccc | atgggaaaat | tgttggcatc | aaagtcacca | atgataccaa | ggaagccctc | 780 |
| attaaccatt | tcaatctgat | gataaacaag | tattttgaag | accatcaagt | ccaacaagca | 840 |
| aagaagtgca | ttcgagagcc | aagatttgtg | gaagttttac | tgccaaatag | tactctatct | 900 |
| gacagatttg | ttattgaagt | ggacattatt | ccacagttct | ctgaatgcca | atatgattat | 960 |
| ttccagatta | aaatgcaaaa | ttacaacaac | aaaatatggg | aacaaagtaa | aaaattctca | 1020 |
| ctatttgtgc | gagatgggac | cagctctaag | gacattacga | aaaataaagt | tgatttcaga | 1080 |
| gcatttaaag | cagattttaa | aacactggca | gagtccagaa | aagcagcaga | agaaaaattc | 1140 |
| agagcaaaaa | caaataaaaa | agaaagagag | ggaccaaagt | tggttaaatt | attgacagga | 1200 |
| aatcaagatt | tgttagataa | ttcatactat | gaacagtaca | ttcttgtaac | aaataaatgc | 1260 |
| cacccagatc | aaacaaaaca | cttagatttc | ctgaaggaaa | ttaaatggtt | tgctgtattg | 1320 |
| gagtttgatc | ctgagtctaa | catcaatgga | gtggtcaaag | cttacaaaga | aagccgagta | 1380 |
| gcaaaccttc | actttccaag | tgtatatgta | gaacagaaaa | ccacaccaaa | tgagacgatt | 1440 |
| tctactctaa | atctttacca | tcaacccagc | tggattttct | gcaatggcag | gttagacctt | 1500 |
| gacagtgaaa | aatataaacc | ctttgatcca | agttcctggc | aaagagaaag | agcttctgat | 1560 |
| gtcaggaaac | tgatttcatt | tcttacacat | gaagacataa | tgccaagagg | gaagttttg | 1620 |
| gtggtatttc | tattactgtc | ctctgtggat | gacccaagag | atcccctcat | tgagactttc | 1680 |
| tgtgctttct | accaggatct | caaaggaatg | gaaaatatac | tgtgtatttg | tgtgcaccca | 1740 |
| cacatatttc | agggatggaa | agatctactt | gaagcaagat | taataaaaca | ccaagatgaa | 1800 |
| atttcaagcc | aatgtatttc | tgctttaagc | cttgaagaga | tcaatggcac | tattcttaaa | 1860 |
| ctaaatctg | tgactcaatc | ttcaaaaagg | cttttgccat | ctattggttt | atcgactgtc | 1920 |
| cttctgaaaa | aggaagaaga | tatcatgact | gctctgaaa | ttatctgtga | aaatgaatgt | 1980 |
| gagggtacac | tgttagagaa | ggacaaaaat | aaattccttg | aattcaaggc | atcaaaagag | 2040 |

```
gaagacttct atcgaggtgg caaagtgtca tggtggaact tctacttctc ttctgaaagt   2100
tattcttcac cttttgtcaa aagggataaa tatgaaagac ttgaagcaat gattcaaaac   2160
tgtgcagatt cttctaaacc aacaagtacc aaaattattc atctgtatca tcatccaggc   2220
tgtgggggaa ctaccttggc tatgcacatt ctctgggaac taaggaagaa attcagatgt   2280
gctgtgctga aaacaagac agtggatttt tctgaaattg gagaacaggt aaccagttta   2340
atcacctatg gggcaatgaa ccgtcaggaa tacgtacctg tactactcct tgttgatgat   2400
tttgaagaac aagataatgt ctatcttctg cagtactcta ttcaaacagc tatagctaaa   2460
aagtacattc gatatgaaaa acctctggtg attatcctaa attgtatgag atcacaaaat   2520
cctgaaaaaa gtgcaaggat cccagacagt attgccgtaa tacagcaact ctctcccaaa   2580
gaacagagag cttttgagct taaattgaaa gaaatcaaag aacagcataa aaactttgag   2640 gattttatt cctttatgat catgaaaacc aattttaata agaatacat agaaaatgtg   2700 gtccggaata tcctgaaagg gcagaatatt ttcaccaagg aagcaaagct cttttctttt   2760
ctggctcttc ttaattcata tgtgcctgat accaccattt cactatcaca gtgtgaaaaa   2820
ttcttaggaa ttggaaacaa gaaggctttc tgggggacag aaaaatttga agacaagatg   2880
ggcacctact ctacaattct gataaaaaca gaggtcatcg aatgtgggaa ctactgtgga   2940
gtacgcatca ttcactcttt gattgcagag ttctcactgg aagaattgaa gaaaagctat   3000
cacctgaata aaagtcaaat tatgttggat atgctaactg agaatttgtt cttcgatact   3060
ggtatgggaa aaagtaaatt tttgcaagat atgcacacac tcctactcac aagacaccgc   3120
gatgaacatg aaggtgaaac aggaaattgg ttttccccat ttattgaagc attacataaa   3180
gatgaaggaa atgaagcagt tgaagctgta ttgcttgaaa gtatccatcg gttcaaccca   3240
aatgcattca tttgccaagc gttggcaaga catttctaca ttaaaaagaa ggactttggc   3300
aatgctctaa actgggcaaa acaagcaaaa atcatagaac ctgacaattc ttatatctca   3360
gatacactgg gtcaagtcta caaaagtaaa ataagatggt ggatagagga aaacggagga   3420
aacgggaaca tttcagttga tgatctaatt gctcttttgg atttagcaga acatgcctca   3480
agtgcattca aagaatctca acagcaaagt gaagatagaa gtatgaagt gaaggaaaga   3540 ttgtatccga agtcaaaaag gcggtatgat acttacaata tagctggtta tcaaggagag   3600
atagaagttg ggctttacac aatccaaatt ctccagctca ttccttttt tgataataaa   3660 aatgagctat ctaaaagata tatggtcaat tttgtatcag gaagtagtga tattccaggg   3720
gatccaaaca atgaatataa attagccctc aaaaactata ttccttattt aactaaattg   3780
aaattttctt tgaaaaagtc ctttgatttt tttgatgaat actttgtcct gctaaaaccc   3840
aggaacaata ttaagcaaaa tgaagaggcc aaaactcgga gaaaggtggc tggatatttt   3900
aagaaatatg tagatatatt ttgtctctta gaagaatcac aaaacaacac aggtcttgga   3960
tcaaagttca gtgagccact tcaagtgagag agatgcagga gaaacctagt agctttaaaa   4020
gcagacaagt tttctgggct cttggaatat cttatcaaaa gtcaagagga tgctataagc   4080
actatgaaat gtatagtgaa cgaatatact tttctcttag aacaatgcac tgtcaaaatc   4140
cagtcaaaag aaaagctaaa tttcatcttg gccaacatta ttctctcctg tatccaacct   4200
acctccagat tagtaaagcc agttgaaaaa ctaaagatc agcttcgaga agtcttgcaa   4260
ccaataggac tgacttatca gttttcagaa ccgtattttc tagcttccct cttattctgg   4320
ccagaaaatc aacaactaga tcaacattct gaacaaatga aagagtatgc tcaagcacta   4380
```

```
aaaaattctt tcaaggggca atataaacat atgcatcgta caaagcaacc aattgcatat        4440
ttctttcttg gaaaaggtaa aagactggaa agacttgttc acaaaggaaa aattgaccag        4500
tgctttaaga agacaccaga tattaattcc ttgtggcaga gtggagatgt gtggaaggag        4560
gaaaaagtcc aagaactttt gcttcgttta caaggtcgag ctgaaaacaa ttgtttatat        4620
atagaatatg gaatcaatga aaaaatcaca atacccatca ctcccgcttt tttaggtcaa        4680
cttagaagtg gcagaagcat agagaaggtg tcttttttacc tgggattttc cattggaggc      4740
ccacttgctt atgacattga aattgtttaa                                        4770

<210> SEQ ID NO 13
<211> LENGTH: 504
<212> TYPE: DNA
<213> ORGANISM: Homo sapiens
<220> FEATURE:
<221> NAME/KEY: misc_feature
<222> LOCATION: (1)..(504)
<223> OTHER INFORMATION: Inverted region of SAMD9 gene (the reverse
      complement of the sequence between the gRNA targets)

<400> SEQUENCE: 13
gcacaaatag tgagaatttt ttactttgtt cccatatttt gttgttgtaa ttttgcattt          60
taatctggaa ataatcatat tggcattcag agaactgtgg aataatgtcc acttcaataa         120
caaatctgtc agatagagta ctatttggca gtaaaacttc cacaaatctt ggctctcgaa         180
tgcacttctt tgcttgttgg acttgatggt cttcaaaata cttgtttatc atcagattga         240
aatggttaat gagggcttcc ttggtatcat tggtgacttt gatgccaaca attttcccat         300
ggggtttgtc tttgactcca aaatgaatag tgccattggt acgtgaattc atacaagctg         360
aagcaaatcg gaaaacctca ttgctaaatt tcatcttgac atcctcttct gtggctgttg         420
ctgtatttgt gaaggctttg aattcatgta tcggatcaat gagattgcct ggtcctgttt         480
caggctgtag actaaaatcc aact                                               504

<210> SEQ ID NO 14
<211> LENGTH: 522
<212> TYPE: DNA
<213> ORGANISM: Homo sapiens
<220> FEATURE:
<221> NAME/KEY: misc_feature
<222> LOCATION: (1)..(522)
<223> OTHER INFORMATION: Portion of SAMD9-null gene containing the
      inversion, identified in B2 clone

<400> SEQUENCE: 14
cgttacatcg cacaaatagt gagaattttt tactttgttc ccatattttg ttgttgtaat          60
tttgcatttt aatctggaaa taatcatatt ggcattcaga gaactgtgga ataatgtcca        120
cttcaataac aaatctgtca gatagagtac tatttggcag taaaacttcc acaaatcttg        180
gctctcgaat gcacttcttt gcttgttgga cttgatggtc ttcaaaatac ttgtttatca        240
tcagattgaa atggttaatg agggcttcct tggtatcatt ggtgactttg atgccaacaa        300
ttttcccatg ggtttgtct ttgactccaa aatgaatagt gccattggta cgtgaattca         360
tacaagctga agcaaatcgg aaaacctcat tgctaaattt catcttgaca tcctcttctg        420
tggctgttgc tgtatttgtg aaggctttga attcatgtat cggatcaatg agattgcctg        480
gtcctgtttc aggctgtaga ctaaaatcca actgagagat gg                           522
```